US011800237B2

(12) United States Patent
Houjou et al.

(10) Patent No.: US 11,800,237 B2
(45) Date of Patent: Oct. 24, 2023

(54) IMAGING DEVICE AND IMAGING METHOD

(71) Applicant: CASIO COMPUTER CO., LTD., Tokyo (JP)

(72) Inventors: Yoshiharu Houjou, Tokyo (JP); Nobuhiro Aoki, Kokubunji (JP); Shigeki Mineo, Hino (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 17/851,606

(22) Filed: Jun. 28, 2022

(65) Prior Publication Data

US 2022/0329721 A1 Oct. 13, 2022

Related U.S. Application Data

(63) Continuation of application No. 16/957,423, filed as application No. PCT/JP2018/047461 on Dec. 25, 2018, now Pat. No. 11,405,561.

(30) Foreign Application Priority Data

Dec. 27, 2017 (JP) ................................. 2017-250772
Mar. 14, 2018 (JP) ................................. 2018-046165

(51) Int. Cl.
*H04N 23/74* (2023.01)
*A61B 5/00* (2006.01)
(Continued)

(52) U.S. Cl.
CPC ........... *H04N 23/74* (2023.01); *A61B 5/0077* (2013.01); *A61B 5/1032* (2013.01); *A61B 5/444* (2013.01);
(Continued)

(58) Field of Classification Search
CPC .. H04N 5/2354; H04N 9/0455; H04N 5/2252; H04N 5/2256; H04N 7/18;
(Continued)

(56) References Cited

U.S. PATENT DOCUMENTS 4,717,952 A 1/1988 Kohayakawa et al.
6,424,858 B1 * 7/2002 Williams ............... A61B 5/489
600/481

(Continued)

FOREIGN PATENT DOCUMENTS

JP 2005249797 A 9/2005
JP 2008237243 A 10/2008
(Continued)

OTHER PUBLICATIONS

International Search Report (ISR) (and English translation thereof) dated Mar. 5, 2019 issued in International Application No. PCT/JP2018/047461.

(Continued)

*Primary Examiner* — Girumsew Wendmagegn
(74) *Attorney, Agent, or Firm* — Holtz, Holtz & Volek PC

(57) ABSTRACT

An imaging device that images a disease site as a subject includes a camera body, a light unit that is provided in the camera body and includes a first light source and a second light source that have different characteristics, and a filter unit that includes at least one independent filter capable of being positioned on and retracted from an optical axis of the camera body. The imaging device performs continuous imaging by imaging in a state in which the subject is illuminated with light from the first light source and, via a first mode, the filter is positioned on or retracted from the optical axis and, thereafter, imaging in a state in which the subject is illuminated with light from the second light source (Continued)

and, via a second mode that differs from the first mode, the filter is positioned on or retracted from the optical axis.

17 Claims, 22 Drawing Sheets

(51) Int. Cl.
    *A61B 5/103*     (2006.01)
    *H04N 7/18*     (2006.01)
    *H04N 23/51*     (2023.01)
    *H04N 23/55*     (2023.01)
    *H04N 23/56*     (2023.01)
    *H04N 25/11*     (2023.01)

(52) U.S. Cl.
    CPC ............. *H04N 7/18* (2013.01); *H04N 23/51* (2023.01); *H04N 23/55* (2023.01); *H04N 23/56* (2023.01); *H04N 25/11* (2023.01)

(58) Field of Classification Search
    CPC .... H04N 5/2254; H04N 5/33; H04N 5/23245; H04N 7/183; A61B 5/1032; A61B 5/0077; A61B 5/444; A61B 5/0035; A61B 5/0037
    See application file for complete search history.

(56) References Cited

U.S. PATENT DOCUMENTS

| | | | |
|---|---|---|---|
| 7,711,252 B2 | 5/2010 | Konno et al. | |
| 7,826,728 B2 | 11/2010 | Konno et al. | |
| 9,345,430 B2 | 5/2016 | Nakamura et al. | |
| 10,481,095 B2 | 11/2019 | Dimitriadis et al. | |
| 10,684,224 B2 | 6/2020 | Dimitriadis et al. | |
| 2004/0201846 A1 | 10/2004 | Mullani | |
| 2014/0240508 A1* | 8/2014 | Gomi | G01J 3/0208 348/162 |
| 2014/0243685 A1* | 8/2014 | Patwardhan | A61B 5/44 600/476 |
| 2015/0036311 A1* | 2/2015 | Mullani | A61B 5/0077 362/230 |
| 2015/0042818 A1* | 2/2015 | Wada | G02B 27/281 348/164 |
| 2015/0223749 A1 | 8/2015 | Park et al. | |
| 2017/0249436 A1 | 8/2017 | Miller et al. | |
| 2019/0269309 A1 | 9/2019 | Onobori | |
| 2020/0281512 A1* | 9/2020 | Grubb | A61B 5/489 |

FOREIGN PATENT DOCUMENTS

| | | | |
|---|---|---|---|
| JP | 2015046698 A | 3/2015 | |
| JP | 2015152601 A | 8/2015 | |
| JP | 2017526899 A | 9/2017 | |
| WO | 2005071372 A1 | 8/2005 | |

OTHER PUBLICATIONS

Written Opinion dated Mar. 5, 2019 issued in International Application No. PCT/JP2018/047461.

\* cited by examiner

IMAGING DEVICE AND IMAGING METHOD

CROSS-REFERENCE TO RELATED APPLICATIONS

This is a Continuation Application of U.S. application Ser. No. 16/957,423, filed on Jun. 24, 2020, and issued as U.S. Pat. No. 11,405,561, on Aug. 2, 2022, which is a 371 National Stage Entry of PCT/JP2018/047461, filed on Dec. 25, 2018, which is based upon and claims the benefit of priority from Japanese Patent Application No. 2017-250772, filed on Dec. 27, 2017, and Japanese Patent Application No. JP 2018-046165, filed on Mar. 14, 2018, the entire contents of all of which are incorporated herein by reference.

TECHNICAL FIELD

The present disclosure relates to an imaging device, and particularly relates to an imaging device and an imaging method for supporting diagnoses of disease sites.

BACKGROUND ART

In recent years, in the field of dermatology, dermoscopy has played an important role in the diagnosis of pigmented skin diseases. Dermoscopy is an examination method in which the structure and distribution of color of the epidermis and the superficial dermis layer is observed. A dermoscope is a non-invasive examination instrument whereby a lesion is magnified about 10-times and is observed in a state in which the lesion is brightly illuminated by a halogen lamp or the like, and the reflection at the skin surface is suppressed by an echo gel, a polarization filter, or the like. Observation methods in which a dermoscope is used are referred to as dermoscopy examinations. In dermoscopy examinations, diffused reflection caused by keratin is reduced and, as such, it is possible to satisfactorily observe pigment distribution from within the epidermis down to the superficial dermis layer (for example, see Patent Literature 1).

However, with the invention described in Patent Literature 1, there is a problem in that imaging operations must be performed twice in two states, namely a state in which an attachment is not attached to the camera, and a state in which the attachment is attached to the camera. Note that, in the foregoing, background art related to skin diseases such as pigmentary skin diseases are described, but the present disclosure is not limited to dermoscopy cameras for skin diseases and can be applied to cases of imaging disease sites caused by more common diseases.

CITATION LIST

Patent Literature

Patent Literature 1: Unexamined Japanese Patent Application Kokai Publication No. 2015-152601

SUMMARY OF INVENTION

Technical Problem

The present disclosure is made with the view of the above situation, and an objective of the present disclosure is to provide an imaging device whereby a plurality of images in which a disease site can be easily observed can be obtained by a simple operation, and an imaging method using the imaging device.

Solution to Problem

One aspect of the present disclosure that achieves the objective described above is:
an imaging device that images a disease site as a subject, the imaging device including:
a camera body;
a light unit that is provided in the camera body and that includes a first light source and a second light source that have mutually different characteristics; and
a filter unit that includes at least one independent filter, and that is capable of positioning the filter on an optical axis of the camera body and retracting the filter from the optical axis of the camera body; wherein
continuous imaging is performed by the camera body imaging, the subject, in a state in which the subject is illuminated with light from the first light source by the light unit and, via a first mode, the filter is positioned by the filter unit on the optical axis of the camera body or retracted by the filter unit from the optical axis of the camera body and, thereafter, by the camera body imaging, the subject, in a state in which the subject is illuminated with light from the second light source by the light unit and, via a second mode that differs from the first mode, the filter is positioned by the filter unit on the optical axis of the camera body or retracted by the filter unit from the optical axis of the camera body.

The other features of the present disclosure are elucidated by the recitations of the present description and the illustrations of the attached drawings.

Advantageous Effects of Invention

According to the present disclosure, a plurality of images in which a disease site can be easily observed can be obtained by simple operations.

DESCRIPTION OF EMBODIMENTS

Hereinafter, embodiments of a camera to which the present disclosure is applied are described while referencing the drawings. Note that, the camera is applied to a dermoscopy camera, which is an imaging device for examining a cancer (melanoma) such as a mole and, more generally, is applied to a close-up camera, which is an imaging device that captures images coming into contact with a subject, and the like. In the present description, an example of a dermoscopy camera is described. Note that, in the present description, the terms "dermoscope" and "dermoscopy" are used to refer respectively to a skin examination magnifier (device) and skin examination by the same magnifier or a use of the same magnifier (action), in a manner similar to the usage of "microscope" (device) and "microscopy" (examination by a microscope or use of a microscope (method)).

Embodiment 1

Overall Configuration of Dermoscopy Camera 10

First, a dermoscopy camera 10 is described as the imaging device according to Embodiment 1. The dermoscopy camera 10 can, under illumination by a light emitting diode (LED) 11a that emits polarized light and an LED 12a that emits unpolarized light that are provided in a light unit 3, sequentially capture and store images of subjects illuminated with polarized light and images of subjects illuminated with unpolarized light by a single shutter operation. The dermoscopy camera 10 can capture two lesion images, including a lesion image illuminated with polarized light and a lesion image illuminated with unpolarized light, in which there are no differences caused by exposure, white balance, external light, and the like, and there is no deviation in the angle of view. Hereinafter, the dermoscopy camera 10 is described in detail.

Figure 1:
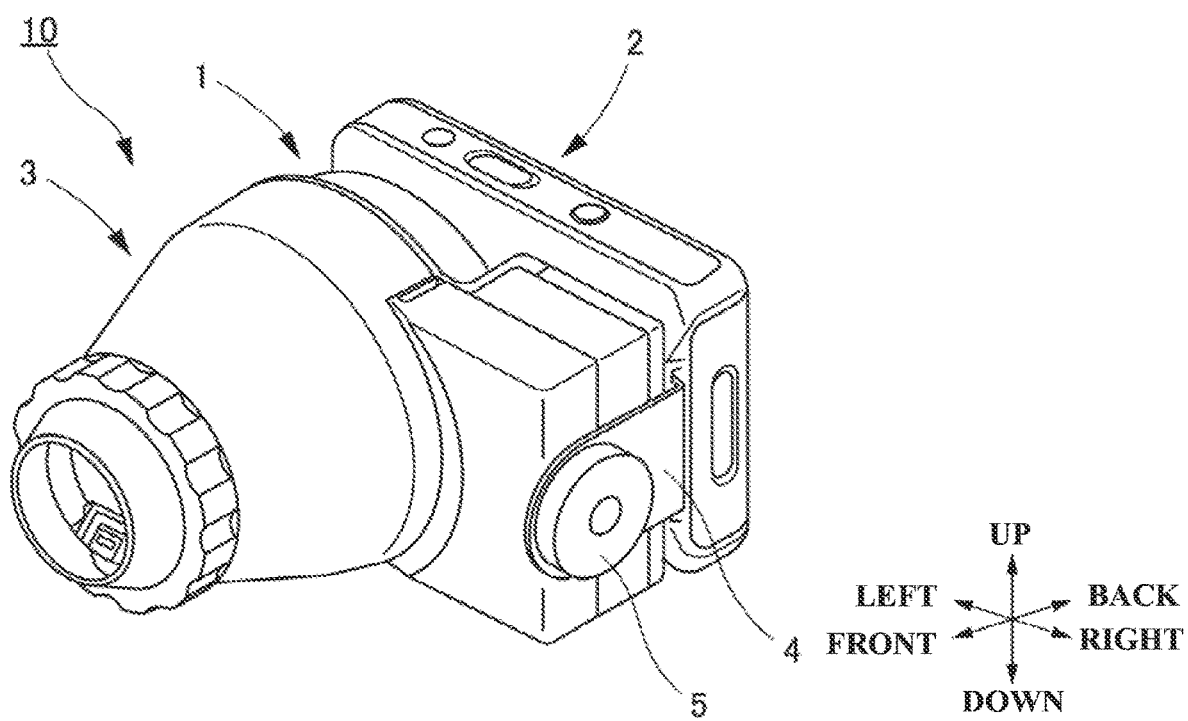
FIG. 1 is a perspective view of an imaging device according to Embodiment 1.
Figure 2:
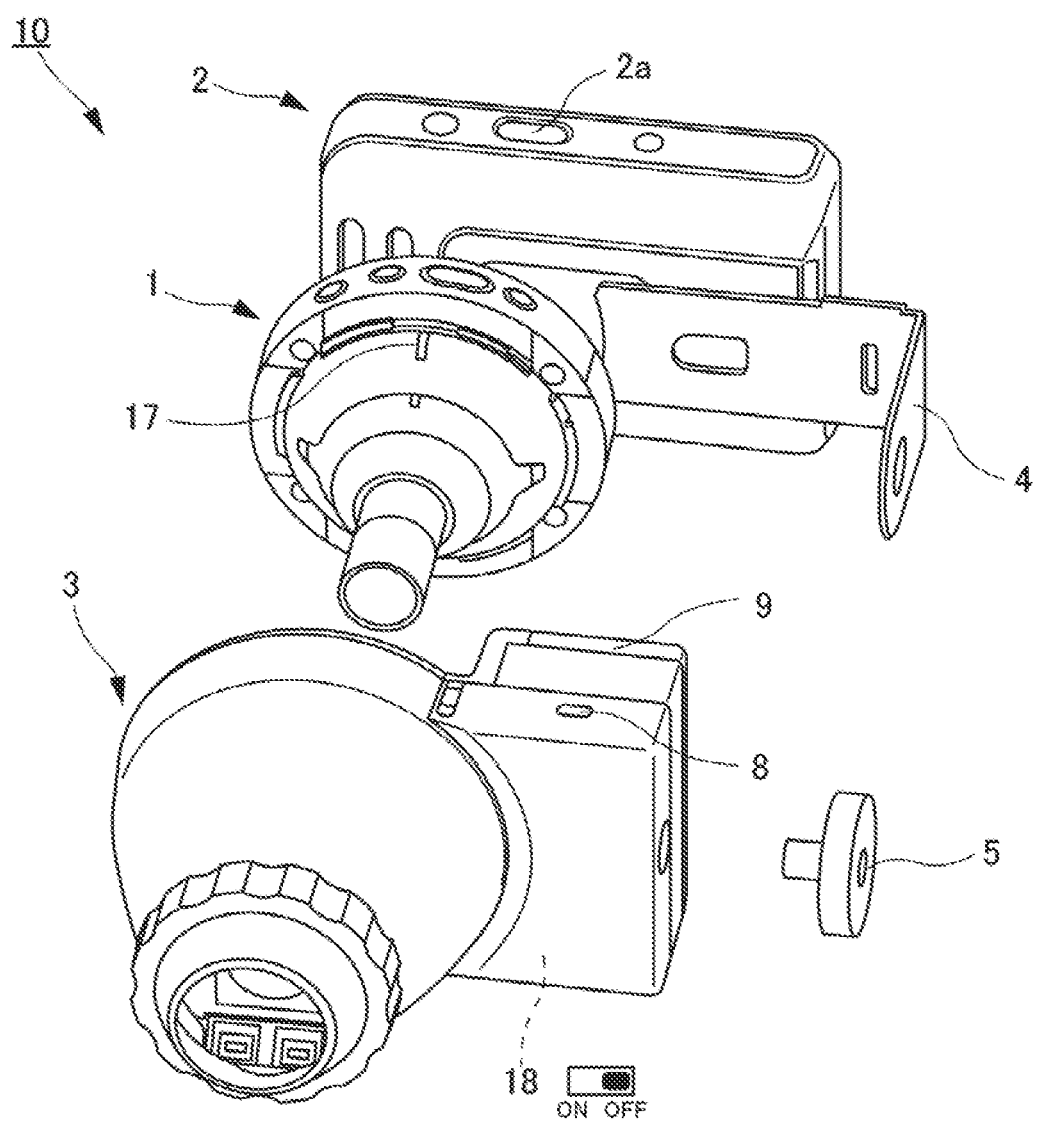
FIG. 2 is a disassembled perspective view of the imaging device according to Embodiment 1.
Figure 3:
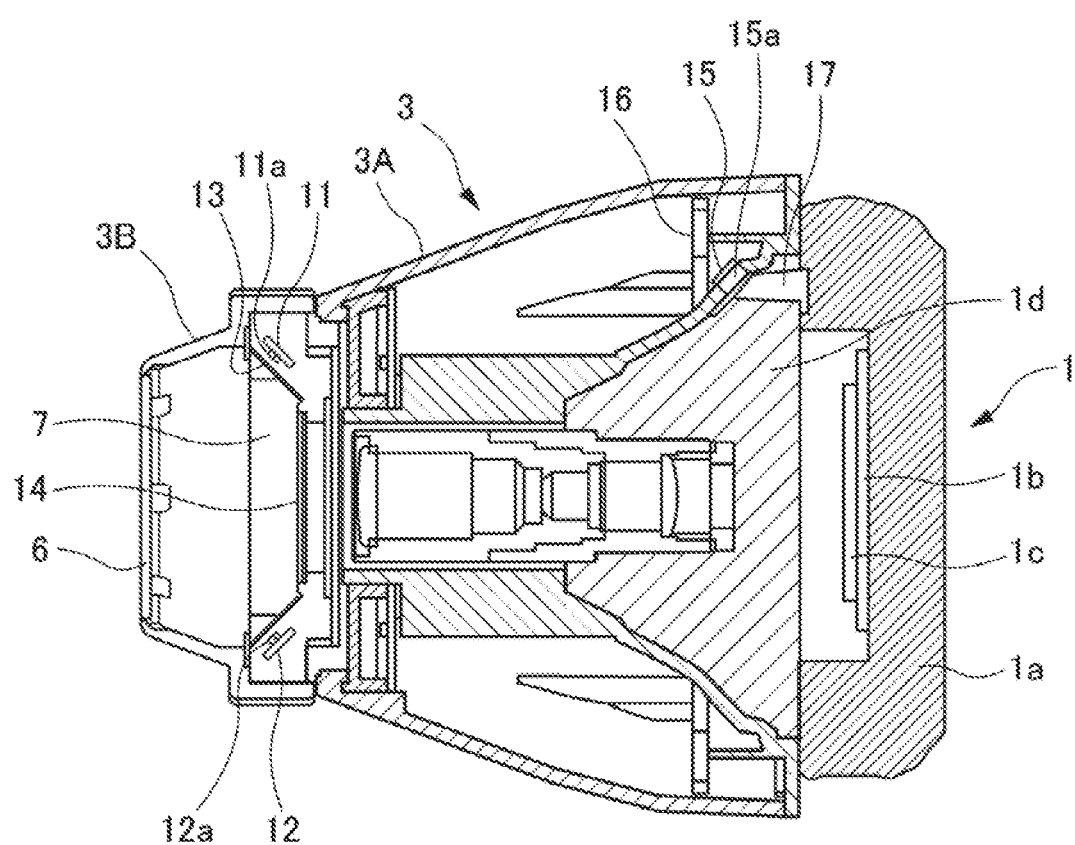
FIG. 3 is a side cross-sectional view explaining a light unit and a camera body according to Embodiment 1.
Figure 4:
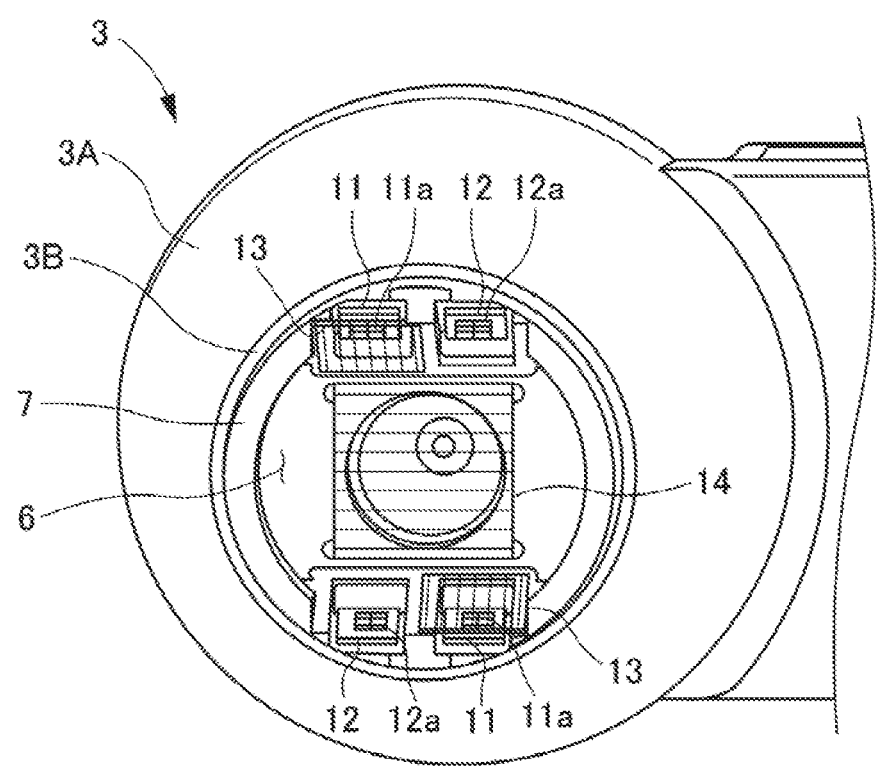
FIG. 4 is a front view explaining the light unit according to Embodiment 1.
Figure 5:
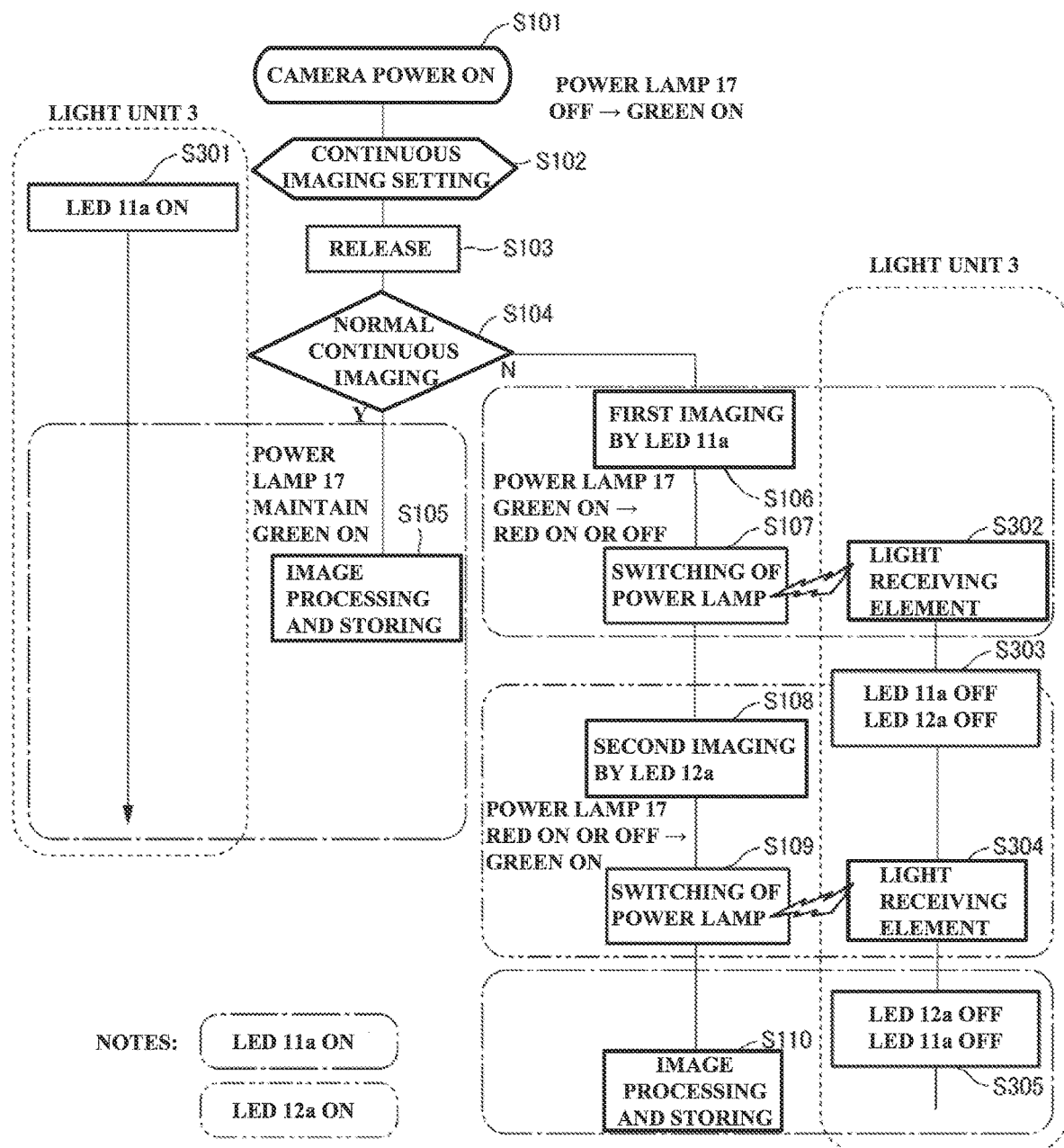
FIG. 5 is a drawing explaining the operation flow of the imaging device according to Embodiment 1.

FIG. 1 is a perspective view of the dermoscopy camera 10 (the imaging device) according to Embodiment 1. FIG. 2 is a disassembled perspective view of the dermoscopy camera 10. FIG. 3 is a side cross-sectional view explaining the light unit 3 and a camera body 1. FIG. 4 is a front view explaining the light unit 3. FIG. 5 is a drawing explaining the operation flow of the dermoscopy camera 10.

Note that, in the following description, as illustrated in FIG. 1, the imaging subject side (that is, the subject side) is defined as the front of the dermoscopy camera 10 (also referred to as the "front surface"), and the side opposite the imaging subject side is defined as the back of the dermoscopy camera 10. The description of the dermoscopy camera 10 is based on a Cartesian coordinate system in which the up, down, left, and right directions are the up, down, left, and right directions when viewing the dermoscopy camera 10 from the front, as-is. Unless mentioned otherwise, the attaching of the various members may be carried out using an appropriate method such as attaching using a normal-sized screw or a small screw and attaching by fitting.

As illustrated in FIG. 1 and FIG. 2, the dermoscopy camera 10 schematically includes a camera body (that is, an imaging device body, also referred to simply as "body") 1, a light unit 3 provided on the front of the camera body 1, and a controller 2 provided on the back of the camera body 1. The light unit 3 illuminates a skin disease site while in a state of contact. Here, the skin disease site is mainly a "mole." The camera body 1 and the light unit 3 are attached to the controller 2 by an attachment stay 4 and a stay fixing screw 5.

A power lamp 17 that indicates a power or charge state of the camera body 1 is provided on the upper side of the camera body 1 in FIG. 2. A power button 8 and a battery 9 of the light unit 3 are provided on the right side of the light unit 3 in FIG. 2. A switch 18 (ON/OFF) is provided on the bottom of the battery 9 of the light unit 3. The switch 18 enables the performance of a continuous imaging operation (described later).

Camera Body 1

As illustrated in FIG. 3, the camera body 1 includes various components such as a housing 1a, an imaging lens system (for example, a zoom lens) 1d, and a circuit wiring board 1b and an imaging element 1c arranged on the back of the imaging lens system 1d. The housing 1a accommodates the various components. As described above, the power lamp 17 that indicates the power or charge state of the camera body 1 is installed on the upper side of the camera body 1 in FIG. 3. The imaging subject side of the imaging lens system 1d is covered by a polarization filter 14. In this case, the polarization filter 14 is provided on the imaging subject side of the imaging lens system 1d, but the polarization filter 14 may be provided between the imaging lens system 1d and the imaging element 1c, or may be provided inside the imaging lens system 1d.

The configuration of a known imaging device used in typical imaging, such as a commercially available digital camera, can be used as the configuration of the camera body 1. For example, known parts can be used as the imaging lens system 1d, the circuit wiring board 1b, and the imaging element 1c. The imaging lens system 1d includes a known optical lens. A charge coupled device (CCD) image sensor or a complementary metal oxide semiconductor (CMOS) image sensor can be used as the imaging element 1c.

Controller 2

As illustrated in FIG. 2, a shutter button 2a is provided on a top surface of the controller 2. Furthermore, a memory unit (not illustrated) in which images that are captured by the imaging element 1c are stored and a control unit (not illustrated) that controls the various components of the dermoscopy camera 10 are provided in the controller 2. A display (not illustrated) that displays the captured images is provided on the back surface of the controller 2. The display may include a touch panel for performing various settings of the dermoscopy camera 10.

Light Unit 3

As illustrated in FIG. 3, the light unit 3 includes a first cover 3A, and a second cover 3B attached to a tip of the first cover 3A. The first cover 3A is formed in a frustoconical cylindrical shape. A light emitter 7 is provided in the second cover 3B. In one example, the first cover 3A and the second cover 3B are formed from a resin such as acrylic resin or a polyvinyl chloride derivative.

The light emitter 7 includes an LED 11a (that is, a first light source) mounted on an LED board 11 and an LED 12a (that is, a second light source) mounted on an LED board 12. Here, a mode is described in which the LED 11a is covered by a polarization filter 13 (LED 11a: LED with polarization filter), and the LED 12a is not covered by a polarization filter. Accordingly, the light emitted from the LED 11a is converted to polarized light by the polarization filter 13, and is emitted on the subject as polarized light. The light emitted from the LED 12a is not polarized by a polarization filter, and is emitted on the subject as unpolarized light. A cover member 6 is fitted into an opening at the tip of the second cover 3B. The cover member 6 contacts the skin disease site, which is the subject, at the time of dermoscopy imaging. The LED 11a and the LED 12a are arranged at positions that do not interfere with the optical axis of the imaging lens system 1d of the camera body 1 (that is, the optical axis of the camera body 1). Since the first cover 3A is formed in a frustoconical cylindrical shape, the light from the LED 11a and the LED 12a is emitted in a tapering manner toward the optical axis of the imaging lens system 1d, in the direction of the skin disease site that is the subject. As a result, the light is concentrated on the skin disease site that is the subject, reflection at the surface of the skin, that is, at the stratum corneum and the epidermis, is suppressed while promoting reflection at the dermis, and the skin disease site can be appropriately imaged.

Note that, here, the LED 11a is referred to as the first light source and the LED 12a is referred to as the second light source. However, in some cases, the term, "light source" is used to refer to a light source, including not only the light emitting element, but also members that affect the characteristics of the light, such as polarization filters, near-infrared filters, infrared cut filters, coloring filters, magnifying lenses, reflection plates, and the like. That is, constituents that create light to be emitted on the subject as illumination light may be referred to as light sources. For example, the LED 11a and the polarization filter 13 covering the LED 11a constitute a single light source, and this light source can be referred to as a light source that includes the LED 11a and the polarization filter 13. Moreover, in this case, an LED (LED 11a) that is covered by a polarization filter and an LED (LED 12a) that is not covered by a polarization filter are provided separately. However, it is possible to switch the light with which the subject is illuminated between polarized light and unpolarized light by moving the polarization filter and positioning the polarization filter in front of the emission surface of one of the LEDs, or retracting the polarization filter from in front of the emission surface of one of the LEDs. Additionally, an exterior member of the LED may be formed from a polarization member.

A window 15a is provided on the upper-right side of the first cover 3A in FIG. 3. Specifically, the window 15a is provided at a position that corresponds to the power lamp 17 of the camera body 1. A photosensor 15 is mounted on the light unit 3 side of the window 15a. The photosensor 15 receives a lighting state of the power lamp 17. The photosensor 15 is connected to an LED control board 16 by a wire, for example. The LED control board 16 is connected to the LED board 11 on which the LED 11a is mounted by a wire, for example. Thus, in the present embodiment, the camera body 1 and the light unit 3 can be linked to the release.

FIG. 4 illustrates the front surface of the light unit 3. FIG. 4 illustrates an example in which a pair of the LED 11a and a pair of the LED 12a are provided at the top and the bottom of the light emitter 7 so as to be staggered with respect to each other. Due to this configuration, unevennesses in the light that the subject is illuminated with can be suppressed. As described later, only the pair of the LEDs 11a turns on when illuminating with polarized light. Additionally, only the pair of the LEDs 12a turns on when illuminating with unpolarized light. Note that, in this case, an example is given in which a pair of the LED 11a and a pair of the LED 12a are provided at the top and the bottom of the light emitter 7 so as to be staggered with respect to each other. However, the pair of the LED 11a and the pair of the LED 12a may be provided on the left and the right, or diagonally, of the light emitter 7 so as to be staggered. That is, equivalent effects can be obtained provided that, when viewing the light unit 3 from the front, the pair of the LED 11a and the pair of the LED 12a are provided with respect to the optical axis of the camera body 1 such that the LEDs of each pair oppose each other.

Note that FIG. 3 and FIG. 4 depict a mode in which the LED 11a is covered by the polarization filter 13 and the LED 12a is not covered by a polarization filter. However, a mode is possible in which both the LED 11a and the LED 12a are covered by polarization filters in anticipation of a case in which the subject is always to be illuminated with polarized light. Moreover, a mode is possible in which both the LED 11a and the LED 12a are not covered by polarization filters in anticipation of a case in which the subject is always to be illuminated with unpolarized light. That is, whether a polarization filter is provided may be determined on the basis on the situation of the skin disease site. Provided that the light emitter 7 of the second cover 3B includes both the LED 11a that is covered by the polarization filter 13 and the LED 12a that is not covered by a polarization filter as illustrated in FIG. 3, by turning the switch 18 illustrated in FIG. 2 ON or OFF, the light source that is turned on can be automatically switched between the LED 11a and the LED 12a when performing continuous imaging, and imaging in which the subject is illuminated with polarized light and imaging in which the subject is illuminated with unpolarized light can be realized by a single shutter operation. Furthermore, in a case in which the polarization filter 13 is attached to one or both of the LED 11a and the LED 12a, the dermoscopy camera 10 can capture an image in which, due to the synergy between the polarization filter 13 and the polarization filter 14, unnecessary reflection from the skin surface is eliminated. As a result, a user is able to examine the skin state on the basis of captured images that are clear.

Operations of Dermoscopy Camera 10

Next, the operation flow of the dermoscopy camera 10 is described while referencing FIG. 5. FIG. 5 illustrates the operation flow of the dermoscopy camera 10, starting from a state in which the LED 11a that is covered by the polarization filter 13 is turned on (step S301 of the light unit 3 illustrated on the left side of FIG. 5).

First, the user sets the power button of the dermoscopy camera 10, which is provided on the controller 2, to the ON state (step S101). As a result, the power lamp 17 of the camera body 1 changes, for example, from an off state to a green lighting state. Next, the user operates the controller 2 to perform continuous imaging setting (step S102). Then, the user presses the shutter button 2a, and the dermoscopy camera 10 is release operated (step S103).

In step S102, in a state in which the power button 8 of the light unit 3 is ON, normal continuous imaging or switching continuous imaging is set on the basis of whether the switch 18 is OFF or ON. Here, the term "normal continuous imaging" means, in a case in which the switch 18 is in the OFF state, continuously imaging by illuminating the subject with light from one of the LED 11a that is covered by the polarization filter 13 and the LED 12a that is not covered by a polarization filter. In contrast, the term "switching continuous imaging" means, in a case in which the switch 18 is the ON state, continuously imaging by automatically switching the light source that is on between the LED 11a that is covered by the polarization filter 13 and the LED 12a that is not covered by a polarization filter.

If the switch 18 is in the OFF state, that is, normal continuous imaging is set to YES at the time of release (step S104; Y), the green lighting state of the power lamp 17 is maintained, the dermoscopy camera 10 continuously captures two images of the subject while illuminating the subject with light from the LED 11a and image-processes and stores the continuously captured images (step S105). Note that, a setting to capture one image may be added in cases in which normal continuous imaging is set to YES. Additionally, when the switch 18 is in the OFF state, continuous imaging may be performed in a light source switching order that differs from the light source switching order when the switch 18 is in the ON state.

Meanwhile, if the switch 18 is in the ON state, that is, normal continuous imaging is set to NO at the time of release (step S104; N), the dermoscopy camera 10 captures a first image while illuminating the subject with light from the LED 11a (step S106). Thereafter, the power lamp 17 changes from the green lighting state to a red lighting state or the off state (step S107). Then, the photosensor 15 (light receiving element) detects the changed state of the power lamp 17 (step S302 of the light unit 3 illustrated on the right side of FIG. 5).

When the photosensor 15 detects the changed state of the power lamp 17, the light unit 3 immediately turns the LED 11a off and turns the LED 12a on (step S303), and matches the timing of turning the LED 12a on to the timing of the second continuous imaging. Then, the dermoscopy camera 10 performs, as continuous imaging, the capturing of the second image while illuminating the subject with light from the LED 12a (step S108). After the second imaging, the power lamp 17 returns to the green lighting state from the red lighting state or the off state (step S109). The photosensor 15 detects the changed state of the power lamp 17 (step S304).

The first image captured while the subject is illuminated with the light from the LED 11a and the second image captured while the subject is illuminated with the light from the LED 12a are image processed and stored as two continuous images (step S110). When the photosensor 15 detects the changed state of the power lamp 17 (step S304), the light unit 3 turns off the LED 12a and turns on the LED 11a, thereby returning to the state of step S301 (step S305).

Thus, the dermoscopy camera 10 according to Embodiment 1 can, by a single shutter operation, perform imaging while the illuminating the subject with the light from the LED 11a that is covered by the polarization filter 13 and imaging while illuminating the subject with the light from the LED 12a that is not covered by a polarization filter. That is, an image with polarized light effects and an image without polarized light effects can be continuously captured by a single shutter operation.

Note that FIG. 5 illustrates an example of continuous imaging by starting the operations from a state in which the LED 11a that is covered by the polarization filter 13 is turned on, and switching the light source that is turned on to the LED 12a that is not covered by a polarization filter as a result of the change in the lighting state of the power lamp 17. However, the dermoscopy camera 10 may operate so as to perform continuous imaging by starting the operations from a state in which the LED 12a that is not covered by a polarization filter is turned on, and switching the light source that is turned on to the LED 11a that is covered by the polarization filter 13 as a result of the change in the lighting state of the power lamp 17. Furthermore, a configuration is possible in which it is possible to select operations that start from the state in which the LED 11a is turned on and operations that start from the state in which the LED 12a is turned on.

Embodiment 2

Next, a dermoscopy camera 20 according to Embodiment 2 is described. In Embodiment 2, the types of LEDs as light sources are increased. Specifically, an LED 211a (first light source) and an LED 212a (second light source) that emit visible light, and an LED 215a that emits near-infrared light are provided. The LED 215a that emits near-infrared light may be replaced with an LED that emits ultraviolet light. As with the dermoscopy camera 10 of Embodiment 1, with the dermoscopy camera 20, the light source that is turned on can be switched at a high-speed. With the dermoscopy camera 20, imaging in which three types of light sources are switched to can be performed by a single shutter operation. The following description focuses on differences with Embodiment 1.

Figure 6:
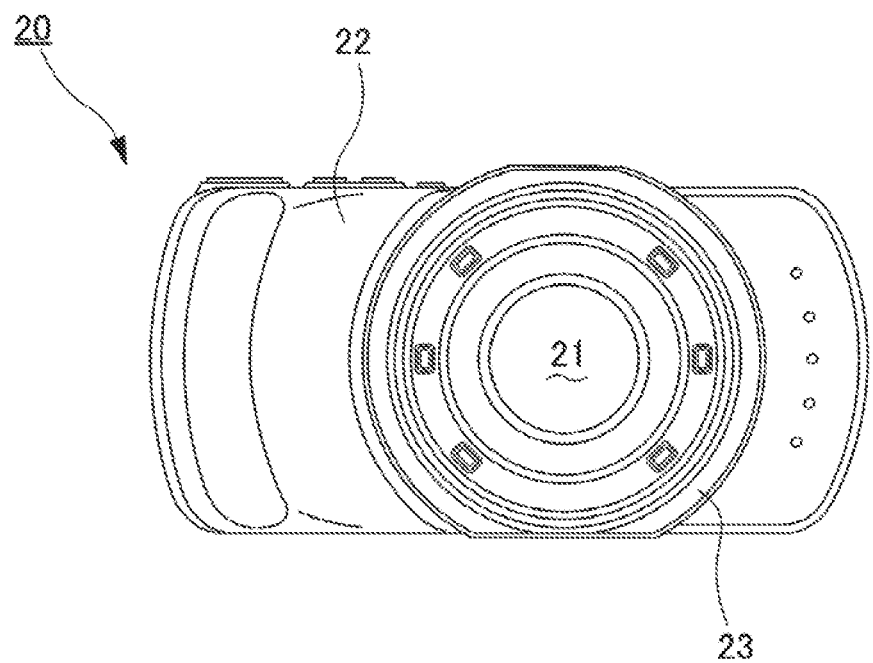
FIG. 6 is a front view of an imaging device according to Embodiment 2.
Figure 7:
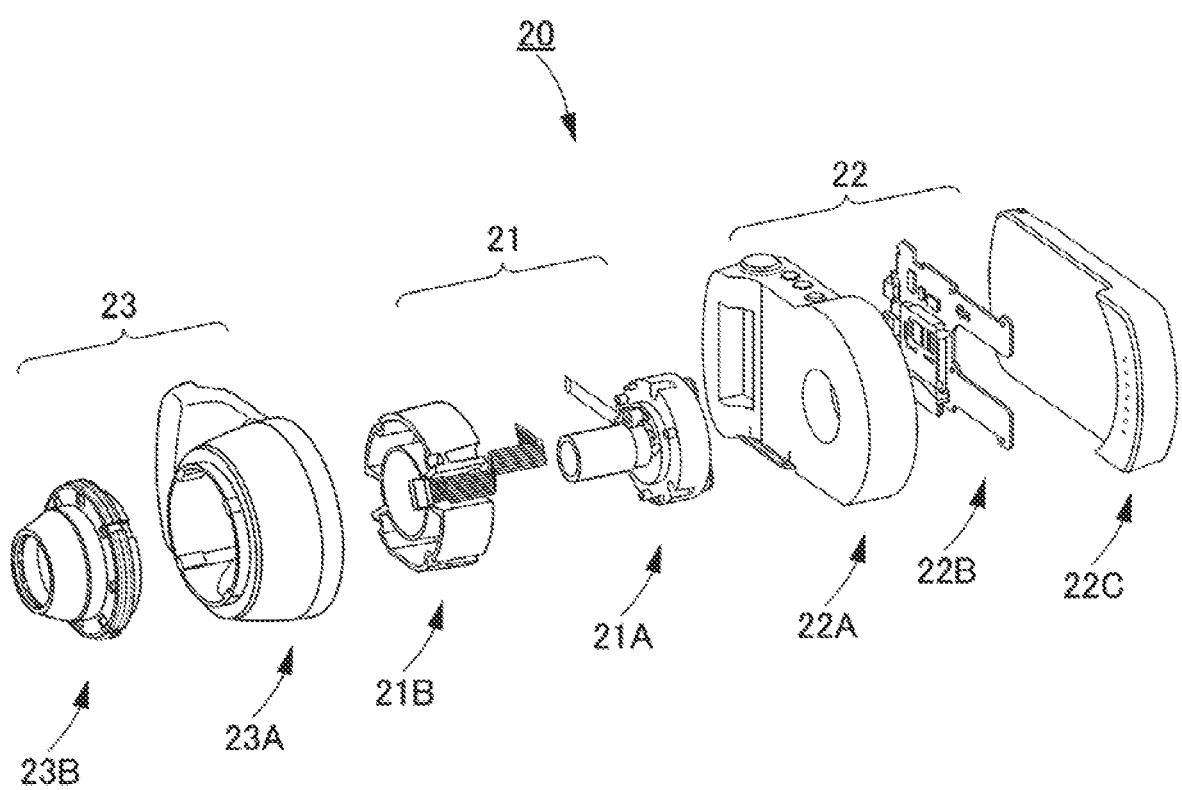
FIG. 7 is a disassembled perspective view of the imaging device according to Embodiment 2.
Figure 8:
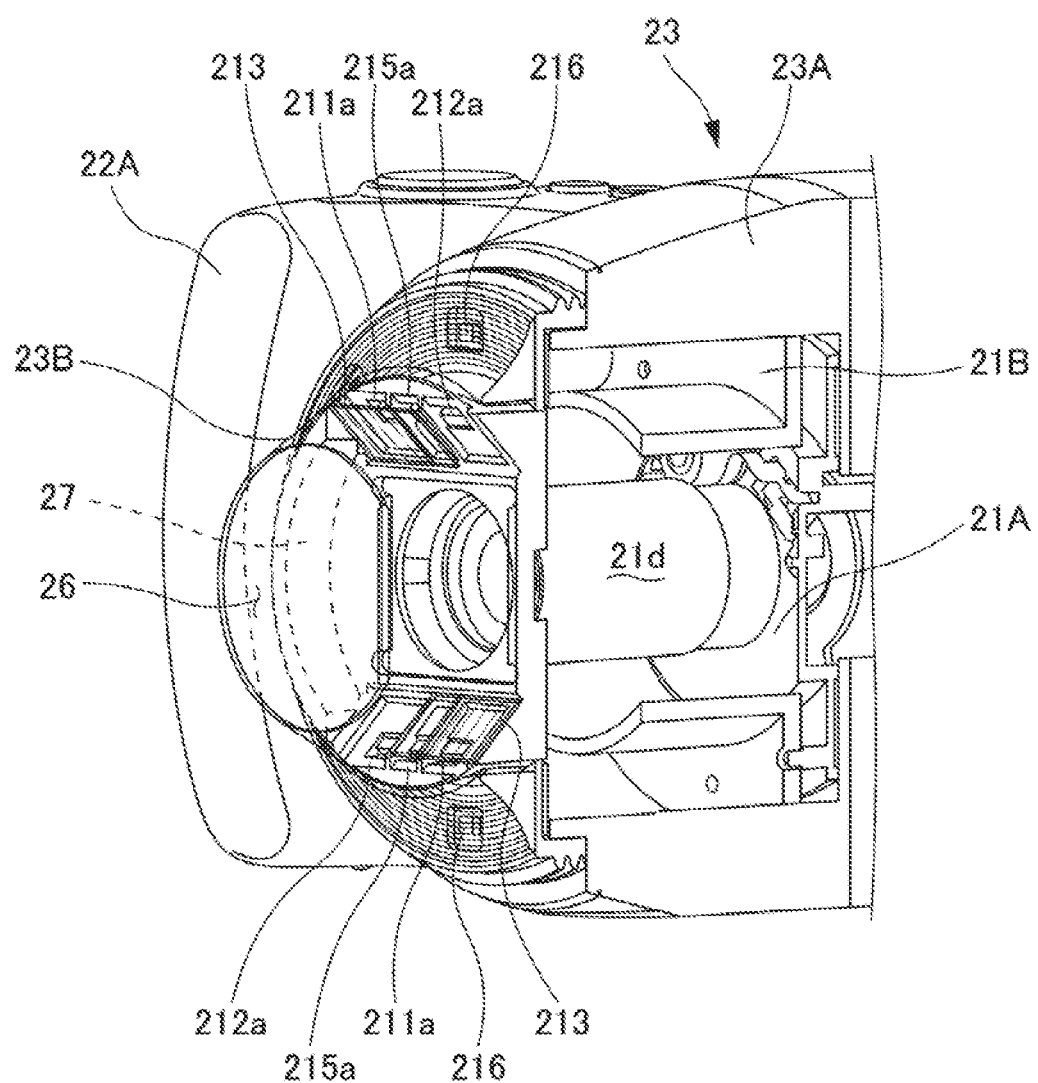
FIG. 8 is a perspective cross-sectional view of a light unit according to Embodiment 2.
Figure 9:
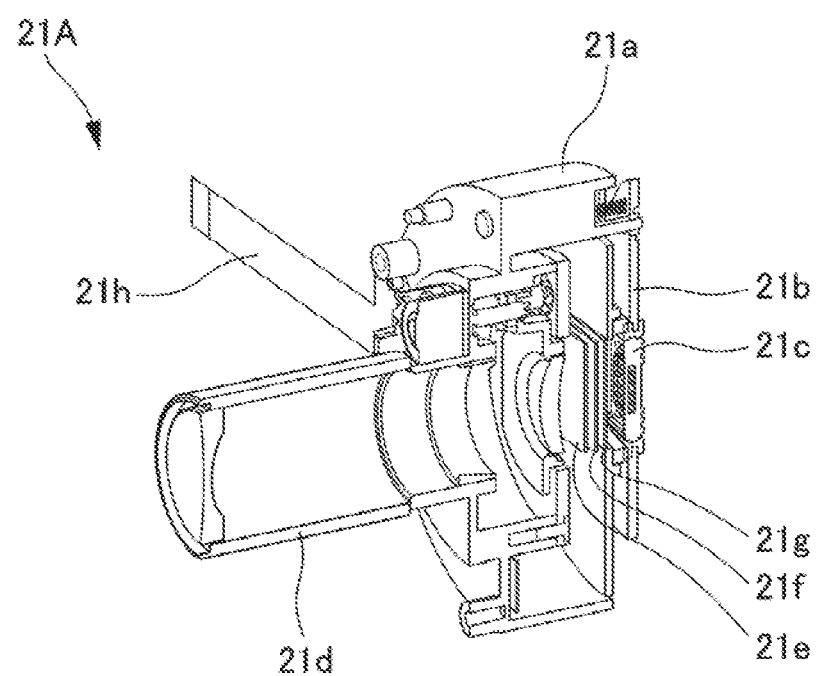
FIG. 9 is a perspective cross-sectional view of a camera body according to Embodiment 2.
Figure 12:
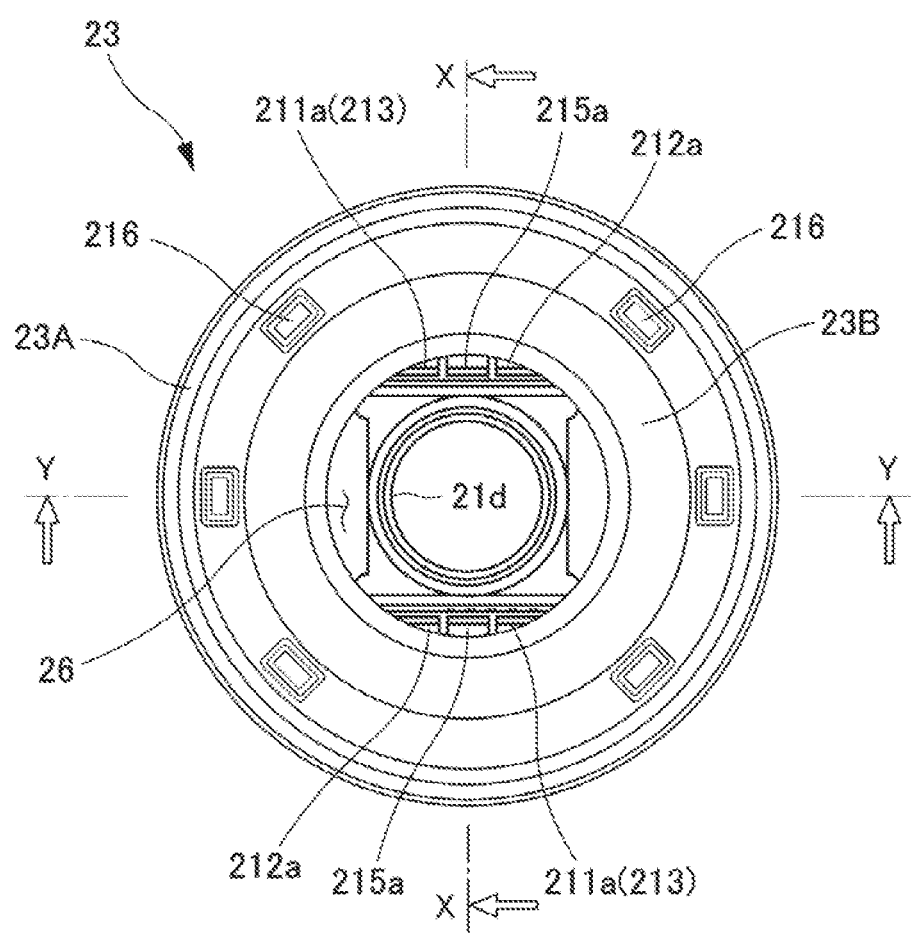
FIG. 12 is a front view of the light unit according to Embodiment 2.
Figure 13:
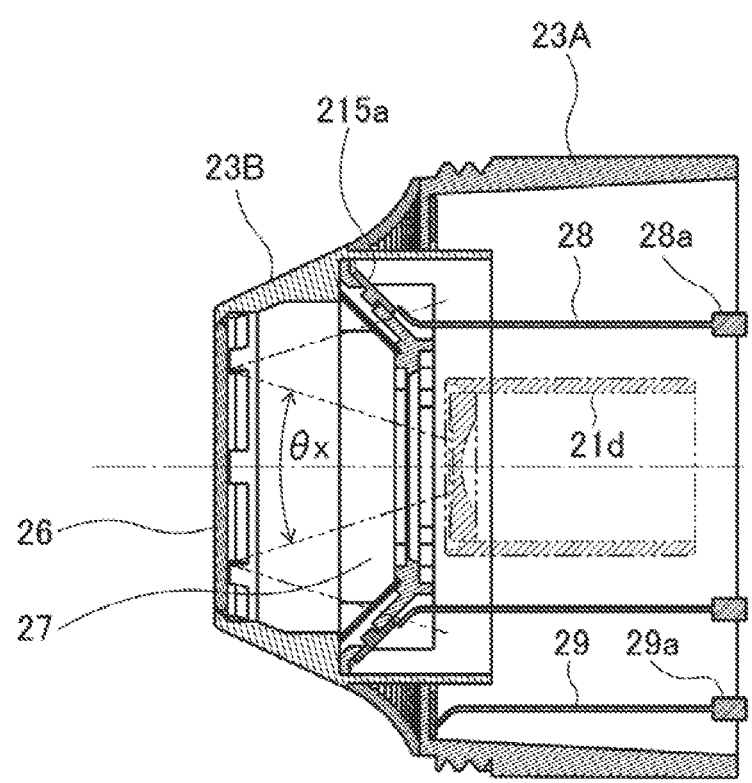
FIG. 13 is cross-sectional view of the light unit depicted in FIG. 12, taken along line X-X.
Figure 14:
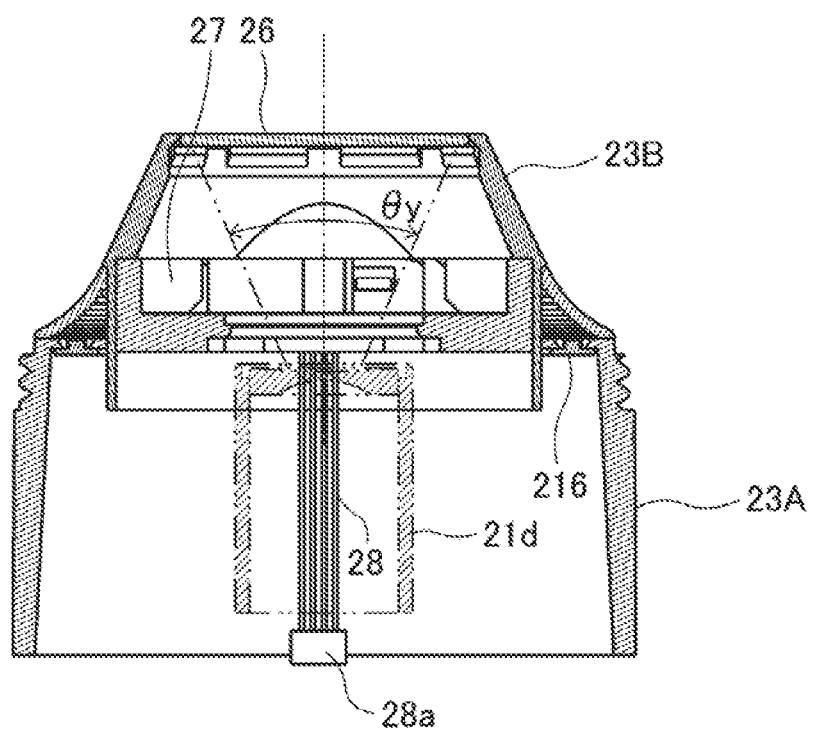
FIG. 14 is a cross-sectional view of the light unit depicted in FIG. 12, taken along line Y-Y.

FIG. 6 is a front view of the dermoscopy camera 20 (the imaging device) according to Embodiment 2. FIG. 7 is a disassembled perspective view of the dermoscopy camera 20. FIG. 8 is a perspective cross-sectional view of a light unit 23. FIG. 9 is a perspective cross-sectional view of a camera body 21. FIG. 12 is a front view of the light unit 23. FIG. 13 is cross-sectional view of the light unit 23 depicted in FIG. 12, taken along line X-X. FIG. 14 is a cross-sectional view of the light unit 23 depicted in FIG. 12, taken along line Y-Y.

As illustrated in FIG. 6, the dermoscopy camera 20 (imaging device) integrally includes a camera body 21, a light unit 23 provided on the front of the camera body 21, and a controller 22 provided on the back of the camera body 21. As illustrated in FIG. 7, the camera body 21 includes a lens unit 21A and a frame 21B. The light unit 23 includes a first cover 23A and a second cover 23B. The controller 22 includes a body 22A, a circuit board 22B, and a display 22C.

The light unit 23 is specifically configured as illustrated in the perspective cross-sectional view of FIG. 8. A first feature of the light unit 23 that differs from the light unit 3 of Embodiment 1 is that a normal imaging LED 216 is provided. The normal imaging LED 216 is used as a light source in normal imaging in which a skin disease site is imaged from a distance without contacting the disease skin site. The normal imaging LED 216 is arranged in an annular manner facing the front, around a base end (back side) of the second cover 23B. FIG. 6 and FIG. 12 (described later) illustrate examples in which a total of six of the normal imaging LEDs 216 are arranged, three on the left and three on the right. Note that while not depicted in entirety, FIG. 8 illustrates an example in which a total of eight of the normal imaging LEDs 216 are arranged.

The normal imaging LED 216 is arranged at equal intervals, concentric with the center of the second cover 23B, and functions as a ring flash that emits light forward from an outer peripheral position of the imaging lens system 21d. The normal imaging LED 216 is formed from an LED that emits white light. A cover member 26 is fitted into an opening at the tip of the second cover 23B. At the time of dermoscopy imaging, the cover member 26 contacts the skin disease site that is the subject.

A second feature of the light unit 23 that differs from the light unit 3 of Embodiment 1 is that a light emitter 27 includes, as dermoscopy imaging light sources, the LED 211a and the LED 212a that emit visible light, and the LED 215a that emits near-infrared light. As in Embodiment 1, the LED 211a, the LED 212a, and the LED 215a are respectively implemented on the top and bottom as pairs. Additionally, the pair of LEDs 211a covered by a polarization filter 213 and the pair of LEDs 212a not covered by a polarization filter are arranged in a staggered manner as in Embodiment 1.

The camera body 21 is attached to the first cover 23A by the frame 21B that surrounds and supports the lens unit 21A. FIG. 9 illustrates a cross-section of the lens unit 21A that is removed from the camera body 21. The circuit wiring board 21b and an imaging element 21c are stored on the back of the imaging lens system 21d, that is, on the back surface of the housing 21a, and an infrared cut filter (IRCF) 21e, a near-infrared transmission filter 21f, and a polarization filter 21g are sequentially arranged, from the front, in front of the imaging lens system 21d. The near-infrared transmission filter 21f is replaced with an ultraviolet transmission filter in cases in which the LED 215a that emits near-infrared light is replaced with an LED that emits ultraviolet light. Note that, a flexible circuit board 21h for operating the lens unit 21A by the controller 22 extends on the left side of FIG. 9.

A desired image can be obtained by combining the polarization filter 21g and a near-infrared transmission filter 21f that matches the polarizing power of the polarization filter 21g. Additionally, by forming the polarization filter 21g from a polarization filter for near-infrared light (near-infrared polarization filter) and combining the polarization filter for near-infrared light 21g with a near-infrared bandpass filter, anti-reflection effects in the near-infrared region can be obtained, near-infrared light can pass through the epidermis of the skin, and the dermis and blood vessels can be appropriately imaged.

Figure 10:
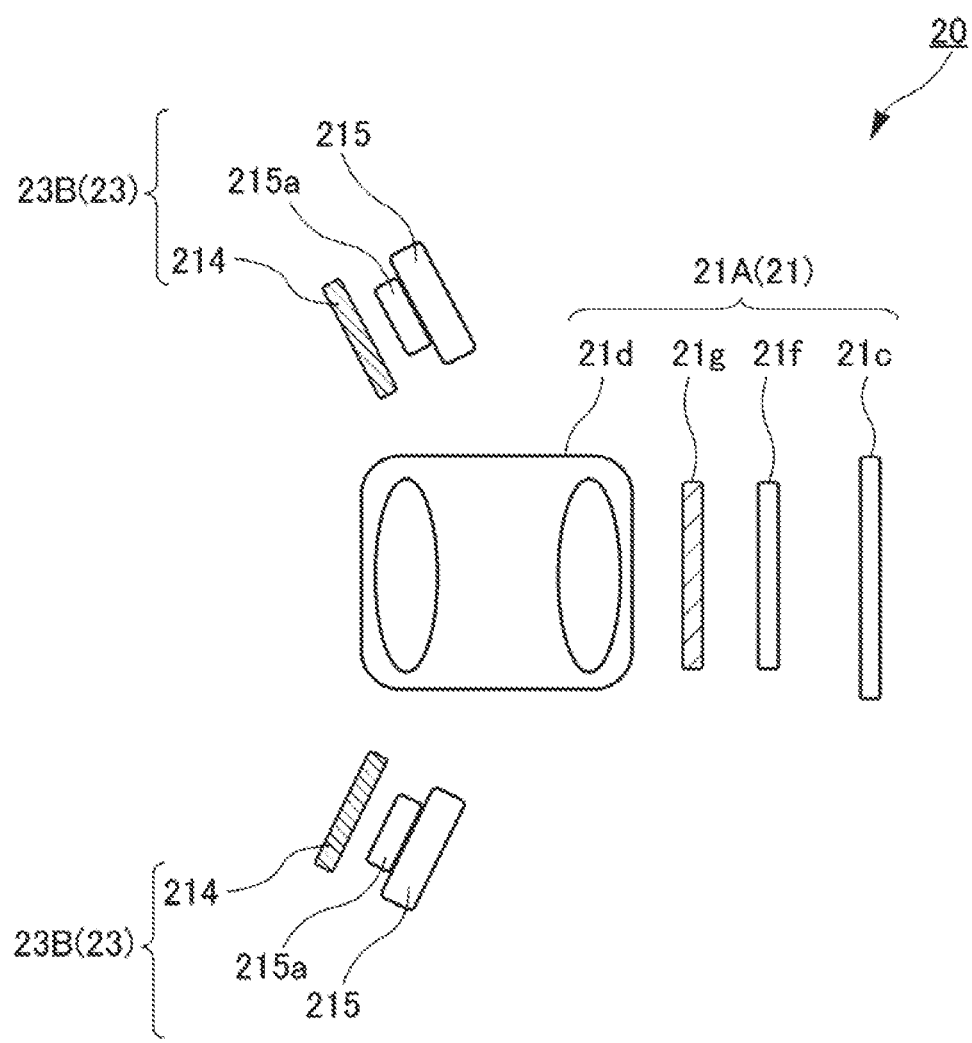
FIG. 10 is a drawing schematically explaining the relationship between the light unit and the camera body (lens unit) according to Embodiment 2.
Figure 11:
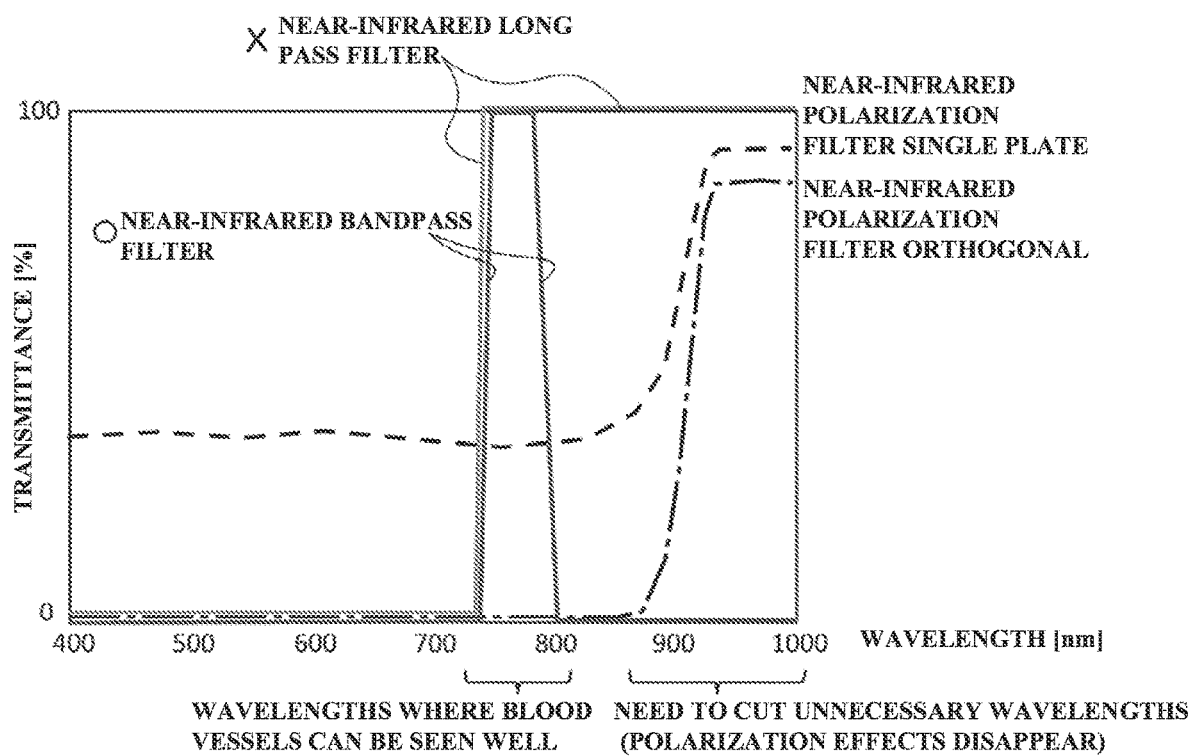
FIG. 11 is a graph explaining the transmittance of a near-infrared polarization filter and a near-infrared transmission filter according to Embodiment 2.

Next, dermoscopy imaging using near-infrared light is described while referencing FIG. 10 and FIG. 11. FIG. 10 is a drawing schematically explaining the relationship between the light unit 23 and the camera body 21 (the lens unit 21A). FIG. 11 is a graph explaining the transmittance of a polarization filter for near-infrared light 214, the polarization filter 21g, and the near-infrared transmission filter 21f.

As described above, near-infrared light is suited for imaging the deepest layer (the dermis) of the skin. Performing dermoscopy imaging using near-infrared light makes it possible to more accurately diagnose lesion of skin disease sites. Therefore, in the present embodiment, as illustrated in FIG. 10, a pair of LEDs 215a that emit near-infrared light is provided on the second cover 23B of the light unit 23. The LEDs 215a are covered by the polarization filter for near-infrared light 214. The polarization filter for near-infrared light 21g and the polarization filter 21f are provided on the lens unit 21A of the camera body 21, on the back of the imaging lens system 21d. Note that, in FIG. 10, the polarization filter 21g and the near-infrared transmission filter 21f are provided in this order from the front, but the near-infrared transmission filter 21f and the polarization filter 21g may be provided in this order from the front.

The near-infrared light emitted from the LED 215a is irradiated on the skin disease site through the polarization filter for near-infrared light 214. The near-infrared light that reflects at the skin disease site enters the imaging lens system 21d of the lens unit 21A. The near-infrared light that enters the imaging lens system 21d passes through the polarizing filter for near-infrared light 21g and the near-infrared light transmission filter 21f, and reaches the imaging element 21c. Here, in cases in which the polarization filter 214 and the polarization filter 21g are linear polarization filters, the polarization filter 214 and the polarization filter 21g are arranged such that the polarization axes thereof are orthogonal to each other.

In this case, if an infrared long pass filter that broadly transmits near-infrared light of a certain wavelength or greater is used as the near-infrared transmission filter 21f, the following defects will occur. Specifically, the transmittance of the polarization filter 214, the near-infrared long pass filter, and the near-infrared bandpass filter are as illustrated in FIG. 11. The polarization filter 21g and the polarization filter 214 for near-infrared light (film type) lose polarization power in the long wavelength region (in the drawing, about 850 nm and greater) regardless of being in a state alone or orthogonal to each other. Meanwhile, the imaging element 21c (for example, a CMOS image sensor) has sensitivity up to about 1000 nm. Thus, if a near-infrared long pass filter that transmits light of about 750 nm and greater, such as that illustrated in FIG. 11, is used as the near-infrared transmission filter 21f, unpolarized light will pass through the near-infrared transmission filter 21f, and unnecessary light (that is, light of unnecessary wavelengths) will enter the imaging element 21c.

Therefore, in the present embodiment, a near-infrared bandpass filter that transmits near-infrared light in the wavelength regions of the polarization filters 214 and 21g (about 700 nm to 800 nm in FIG. 11) is used as the near-infrared transmission filter 21f. As a result, unpolarized light in unnecessary wavelength regions can be removed and images, of wavelength regions where blood vessels of skin disease sites can be seen well, can be reliably captured.

Next, reasons are described about why it is preferable to perform dermoscopy imaging in which the subject is illuminated with near-infrared light and dermoscopy imaging in which the subject is illuminated with ultraviolet light in addition to dermoscopy imaging in which the subject is illuminated with visible light when diagnosing a skin disease site. Since, for example, light of shorter wavelengths cannot reach the deep layers of the skin, dermoscopy imaging in which the subject is illuminated with near-infrared light is suited for imaging of the deepest layer (dermis) of the skin. Meanwhile, with hemangionas, in some cases, the hemoglobin is a pigment that causes changes in the color of the skin disease site and, as such, dermoscopy imaging in which the subject is illuminated with visible light is preferable for the imaging of hemangionas as it is possible to image the color change caused by the oxyhemoglobin. With pigment lesions, in some cases the melanin is a pigment that causes changes in the color of the skin disease site and the absorbance of dopamelanin decreases with light of longer wavelengths. As such, dermoscopy imaging in which the subject is illuminated with ultraviolet light is preferable for the imaging of pigment lesions. Therefore, when diagnosing skin disease sites, it is preferable to perform dermoscopy imaging in which near-infrared light is emitted, dermoscopy imaging in which visible light is emitted, and dermoscopy imaging in which ultraviolet light is emitted.

As illustrated in FIG. 12, the light unit 23 includes the LED 215a, the LED 211a, the LED 212a, and the LED 216 as light sources. The light unit 23 can turn on the light sources in four lighting patterns by control means such as those described in Embodiment 1. In one example, a first pattern is a pattern in which the pair of LEDs 215a that emit near-infrared light (or ultraviolet light) is turned on. A second pattern is a pattern in which the pair of LEDs 211a that is covered by the polarization filter 213 and that emits visible light is turned on. A third pattern is a pattern in which the pair of LEDs 212a that is not covered by a polarization filter and that emits visible light is turned on. The first pattern to the third pattern are used in dermoscopy imaging. A fourth pattern includes is a pattern in which the normal imaging LED 216 is turned on.

Accordingly, the dermoscopy camera 20 can turn on the light sources (LEDs 215a, 211a, 212a) in the first pattern, the second pattern, and the third pattern by a single shutter operation, and can automatically continuously capture images corresponding to the light with which the subject is illuminated. Furthermore, the dermoscopy camera 20 can automatically perform continuous imaging for cases in which the light source is turned on in the fourth pattern.

FIG. 13 illustrates a cross-section (vertical cross-section) of the light unit 23 depicted in FIG. 12, taken along line X-X. In FIG. 13, θx represents a vertical angle of view in dermoscopy imaging in which the light source is turned on in the first pattern, the second pattern, or the third pattern. In the vertical cross-section, the LED 215a, the LED 211a, and the LED 212a emit light in a tapered shape toward the optical axis of the imaging lens system 21d. Accordingly, in the vertical cross-section, the angle at which the reflected light from the skin disease site, which is in contact with the cover member 26, can enter the imaging lens system 21d is small with respect to the optical axis of the imaging lens system 21d, and the vertical angle of view Ox is relatively narrower. In one example, the vertical angle of view Ox of the light unit 23 illustrated in FIG. 13 is 35.2°.

In FIG. 13, a cable 28 and a terminal 28a for inputting a control signal into the LED 215a are provided on the first cover 23A. Additionally, a cable 29 and a terminal 29a for inputting a control signal into the LED 216 illustrated in FIG. 14 are provided near the outer periphery of the first cover 23A. Note that, cables and terminals for inputting control signals to the LED 211a and the LED 212a are also provided on the first cover 23A.

FIG. 14 illustrates a cross-section (horizontal cross-section) of the light unit 23 depicted in FIG. 12, taken along line Y-Y. In FIG. 14, θy represents a horizontal angle of view in dermoscopy imaging in which the light source is turned on in the first pattern, the second pattern, or the third pattern. In the horizontal cross-section, the LED 215a, the LED 211a, and the LED 212a emit light in parallel to the optical axis of the imaging lens system 21d. Accordingly, in the horizontal cross-section, the angle at which the reflected light from the skin disease site, which is in contact with the cover member 26, can enter the imaging lens system 21d is large with respect to the optical axis of the imaging lens system 21d, and the horizontal angle of view Oy is relatively wide. In one example, the horizontal angle of view Oy of the light unit 23 illustrated in FIG. 14 is 47°.

Embodiment 3

Next, a dermoscopy camera 30 (imaging device) according to Embodiment 3 is described. The dermoscopy cameras 10 and 20 according to Embodiment 1 and Embodiment 2 continuously capture, by a single shutter operation, an image illuminated with polarized light and an image illuminated with unpolarized light by switching the light source between a lighting pattern using the LEDs 11a and 211a and a lighting pattern using the LEDs 12a and 212a. However, the dermoscopy camera 30 according to the present embodiment continuously captures an image illuminated with polarized light and an image illuminated with unpolarized light by a combination of switching the lighting patterns of the light sources and moving a polarization filter 31g.

In Embodiment 3, a filter unit 31 that includes a plurality of filters 31A is provided inside the lens unit 21A. The filter unit 31 positions each of the plurality of filters 31A independently on the optical axis of the imaging lens system 21d (camera body 21) or retracts each of the plurality of filters 31A from the optical axis of the imaging lens system 21d. Hereinafter, the configuration and the operations of the filter unit 31 are described while referencing FIGS. 15 to 20. Note that the configurations other than those of the filter unit 31 are the same as in Embodiment 2 and, as such, in the following description, reference is made to FIGS. 6 to 14 as necessary.

As illustrated in FIG. 8, the light unit 23 includes the LED 211a (first light source) and the LED 212a (second light source) that emit visible light for dermoscopy imaging. Furthermore, the light unit 23 includes the LED 215a that emits near-infrared light. The LED 215a that emits near-infrared light may be replaced with an LED that emits ultraviolet light. The LED 215a is covered by the polarization filter 214, and the light from the LED 215a is emitted on the subject as polarized light. The LED 211a is covered by the polarization filter 213, and light from the LED 211a is emitted on the subject as polarized light. The LED 212a is not covered by a polarization filter, and light from the LED 212a is emitted on the subject as unpolarized light. Additionally, the normal imaging (clinical imaging) LED 216 is arranged at an equal interval, concentric with the center of the second cover 23B. The LED 216 functions as a ring flash that emits light forward from an outer peripheral position of the imaging lens system 21d.

Figure 15:
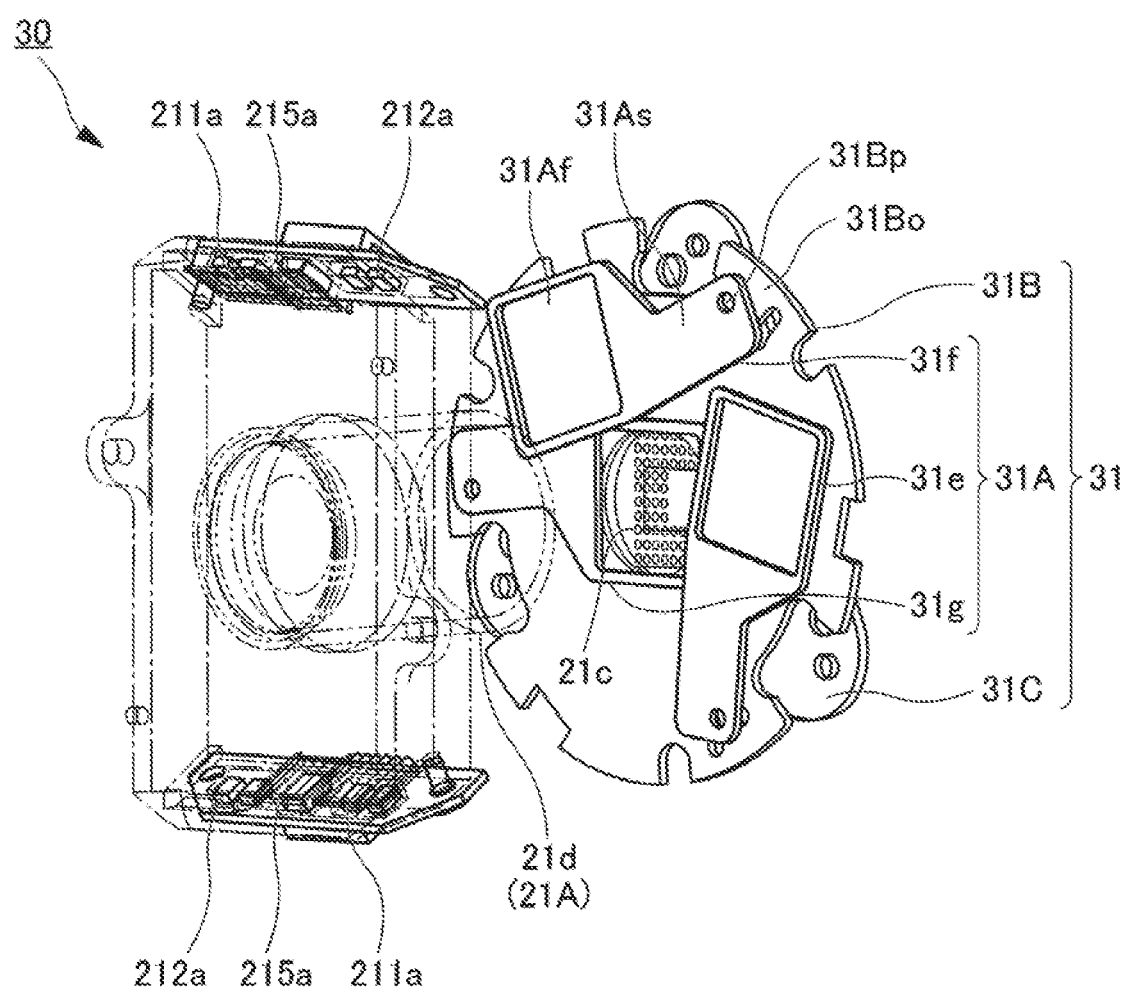
FIG. 15 is a partial perspective view of an imaging device according to Embodiment 3.

As illustrated in FIG. 15, the filter unit 31 includes the plurality of filters 31A, and a filter attachment plate 31B to which the plurality of filters 31A are attached. The filter attachment plate 31B is provided on the back surface (that is, on the imaging element 21c side) of the imaging lens system 21d of the lens unit 21A. The filter attachment plate 31B is fixed to the lens unit 21A via a fixer 31C. The filter unit 31 is provided at a position similar to that of the infrared cut filter 21e, the near-infrared transmission filter 21f, and the polarization filter 21g of Embodiment 2 but, as described hereinafter, the configuration of the filter unit 31 differs from the infrared cut filter 21e, the near-infrared transmission filter 21f, and the like. Note that the filter unit 31 may be provided on the subject side of the imaging lens system 21d. In the present embodiment, the filter unit 31 is provided behind the imaging lens system 21d, that is, immediately before the imaging element 21c in order to ensure the implementation efficiency (implementation space, arrangement of operation mechanism, and the like) of the filter unit 31.

As illustrated in FIG. 15, the filter unit 31 includes three filters as the plurality of filters 31A, namely an infrared cut filter 31e, a near-infrared transmission filter 31f, and a polarization filter 31g. In this case, the filter unit 31 includes three filters as the plurality of filters 31A, but the number of filters is not limited to three. As necessary, the filter unit 31 may, for example, include five or six filters as the plurality of filters 31A. Additionally, the filter unit 31 may include a far-infrared transmission filter, an ultraviolet transmission filter, or the like instead of the near-infrared transmission filter 31f. Moreover, the filter unit 31 may include only the single polarization filter 31g.

Each of the plurality of filters 31A includes filter 31Af that covers the center of the filter attachment plate 31B (that is, the optical axis of the imaging lens system 21d), and a shaft 31As for attaching the filter 31Af to an outer periphery 31Bo of the filter attachment plate 31B. The base end of the shaft 31As is pivotably supported on the outer periphery 31Bo of the filter attachment plate 31B by a pin 31Bp. Due to this configuration, each of the plurality of filters 31A is capable of rotating around the pin 31Bp. Moreover, each of the plurality of filters 31A can, by rotating, be independently positioned on the optical axis of the imaging lens system 21d or be retracted from the optical axis of the imaging lens system 21d.

As described later, each of the plurality of filters 31A is rotates independently on the basis of a continuous imaging setting. Known technology for rotating a filter in conjunction with the operation of the shutter can be used for the mechanism that rotates each of the plurality of filters 31A. Note that the operation of the plurality of filters 31A may be a slide operation (sliding door operation), an open-close operation (hinged door operation), or the like. However, from the perspectives of reducing the space of the dermoscopy camera 30, structural simplicity, and the like, it is preferable that the movement of the plurality of filters 31A be rotation operation.

Figure 16:
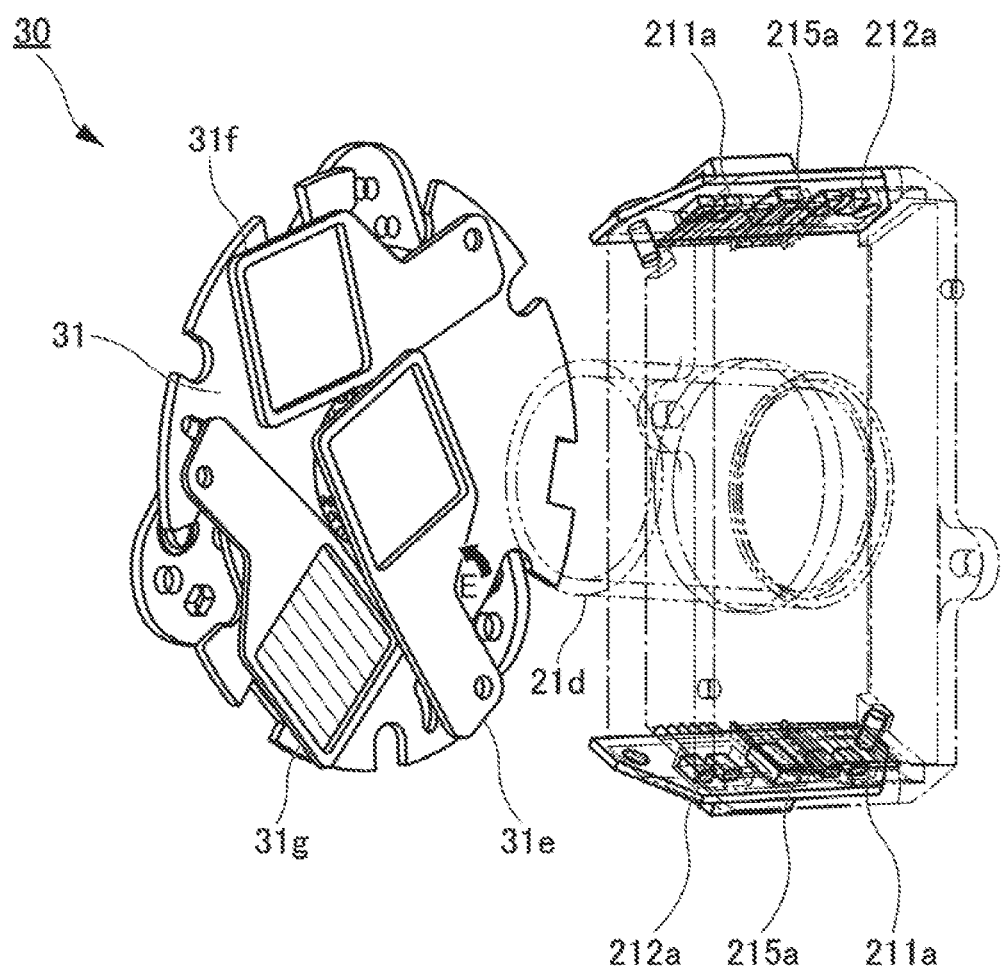
FIG. 16 is a drawing illustrating a first operation mode of a filter unit according to Embodiment 3.

An example is described in which the plurality of filters 31A are operated in response to the turning on of the LEDs 211a, 212a, and 215a of the light unit 23. A first operation mode is an operation of the plurality of filters 31A in imaging in which the subject is illuminated with unpolarized light when performing dermoscopy imaging. In this case, the LED 212a that emits unpolarized visible light is turned on. As illustrated in FIG. 16, in response to the turning on of the LED 212a, the infrared cut filter 31e is rotated in the direction of arrow E, thereby positioning the infrared cut filter 31e on the optical axis of the imaging lens system 21d.

Figure 17:
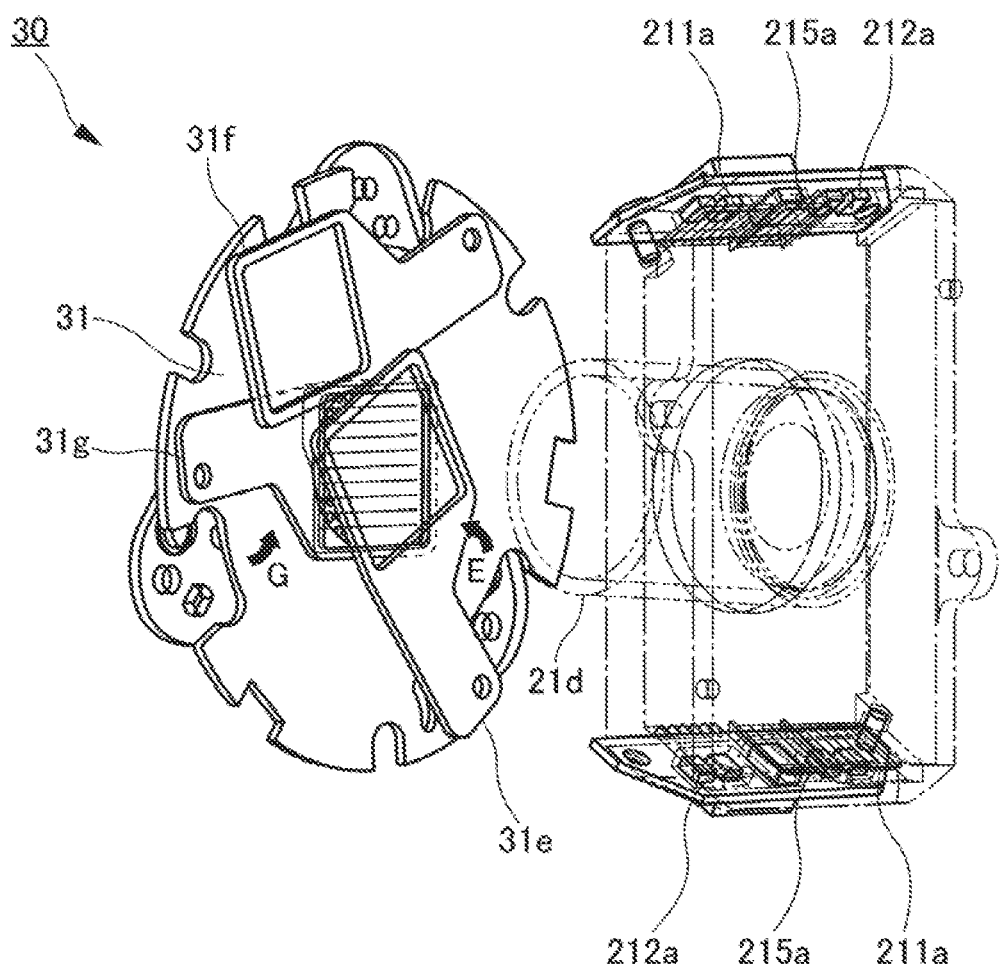
FIG. 17 is a drawing illustrating a second operation mode of the filter unit according to Embodiment 3.

A second operation mode is an operation of the plurality of filters 31A in imaging in which the subject is illuminated with polarized light when performing dermoscopy imaging. In this case, instead of the LED 212a, the LED 211a that is covered by the polarization filter 213 and that emits visible light is turned on. As illustrated in FIG. 17, in response to the turning on of the LED 211a, the infrared cut filter 31e is rotated in the direction of arrow E and the polarization filter 31g is rotated in the direction of arrow G, thereby positioning the infrared cut filter 31e and the polarization filter 31g on the optical axis of the imaging lens system 21d.

A third operation mode is an operation of the plurality of filters 31A when performing normal imaging. In this case, the normal imaging LED 216 is turned on. In response to the turning on of the LED 216, the infrared cut filter 31e is rotated, thereby positioning the infrared cut filter 31e on the optical axis of the imaging lens system 21d.

Figure 18:
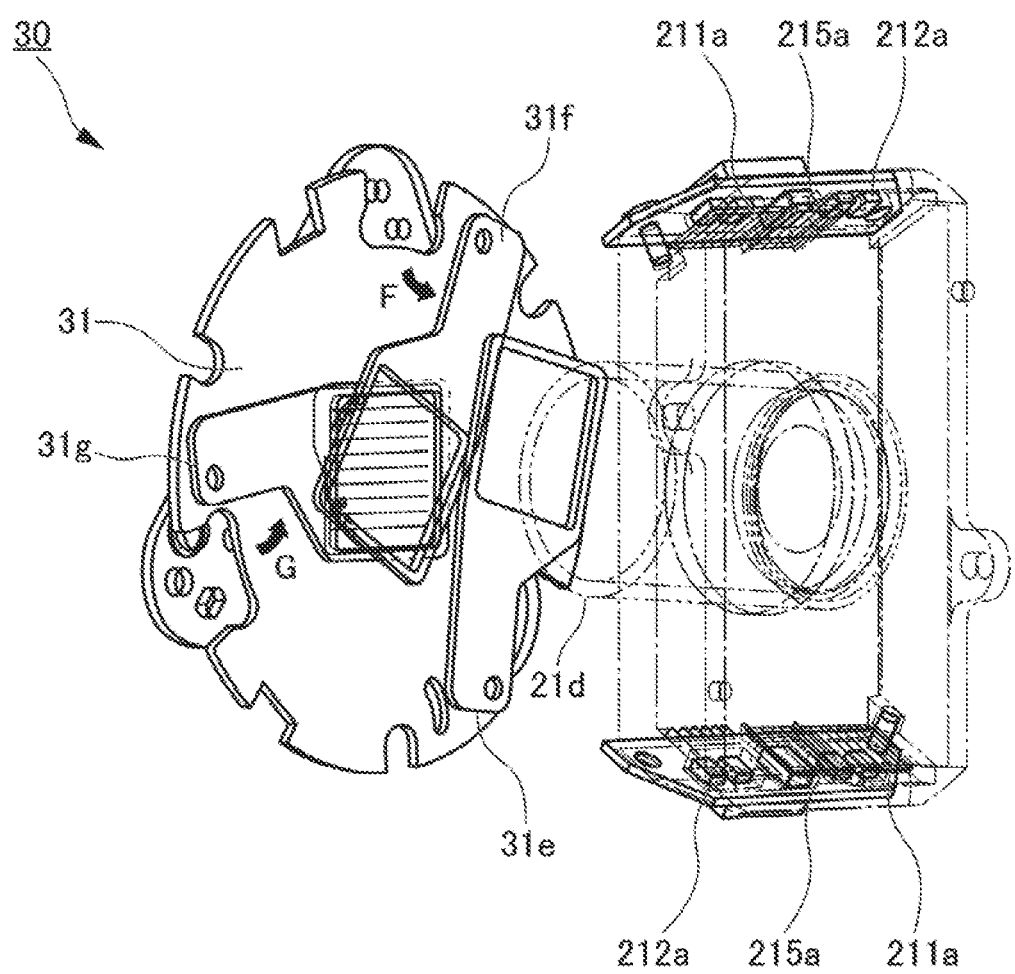
FIG. 18 is a drawing illustrating a fourth operation mode of the filter unit according to Embodiment 3.

A fourth operation mode is an operation of the plurality of filters 31A in imaging in which the subject is illuminated with near-infrared polarized light to perform dermoscopy imaging. In this case, the LED 215a that is covered by the polarization filter 214 and that emits near-infrared light is turned on. As illustrated in FIG. 18, in response to the turning on of the LED 215a, the polarization filter 31g is rotated in the direction of arrow G, and the near-infrared transmission filter 31f is rotated in the direction of arrow F, thereby positioning the polarization filter 31g and the near-infrared transmission filter 31f on the optical axis of the imaging lens system 21d.

In the first operation mode to the third operation mode in which the LEDs 212a, 211a, and 216 that emit visible light are turned on, the infrared cut filter 31e is positioned on the optical axis of the imaging lens system 21d. As a result, it is possible to suppress the red coloring (infrared portions) that occurs in digital images. Note that, when, as in the fourth operation mode, turning on the LED 215a that emits near-infrared light to illuminate the subject with near-infrared light, it is possible to also rotate the infrared cut filter 31e in order to retract the infrared cut filter 31e from the optical axis of the imaging lens system 21d. In the case of imaging in which the subject is illuminated with light other than visible light, it is preferable that, as in the fourth operation mode, the infrared cut filter 31e is retracted from the optical axis of the imaging lens system 21d.

Operations of Dermoscopy Camera 30

Figure 19:
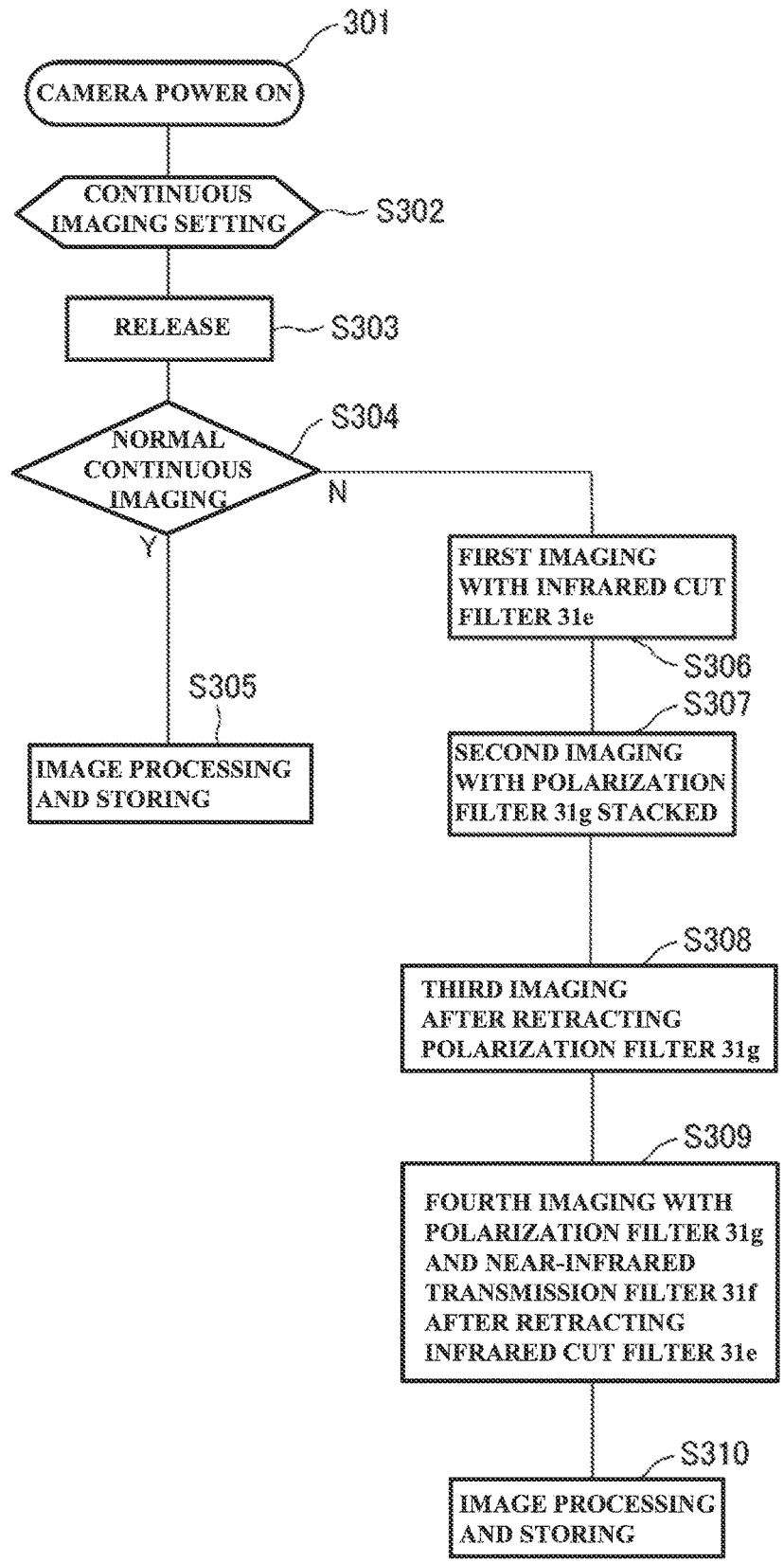
FIG. 19 is a drawing explaining the operation flow of the filter unit according to Embodiment 3.
Figure 20:
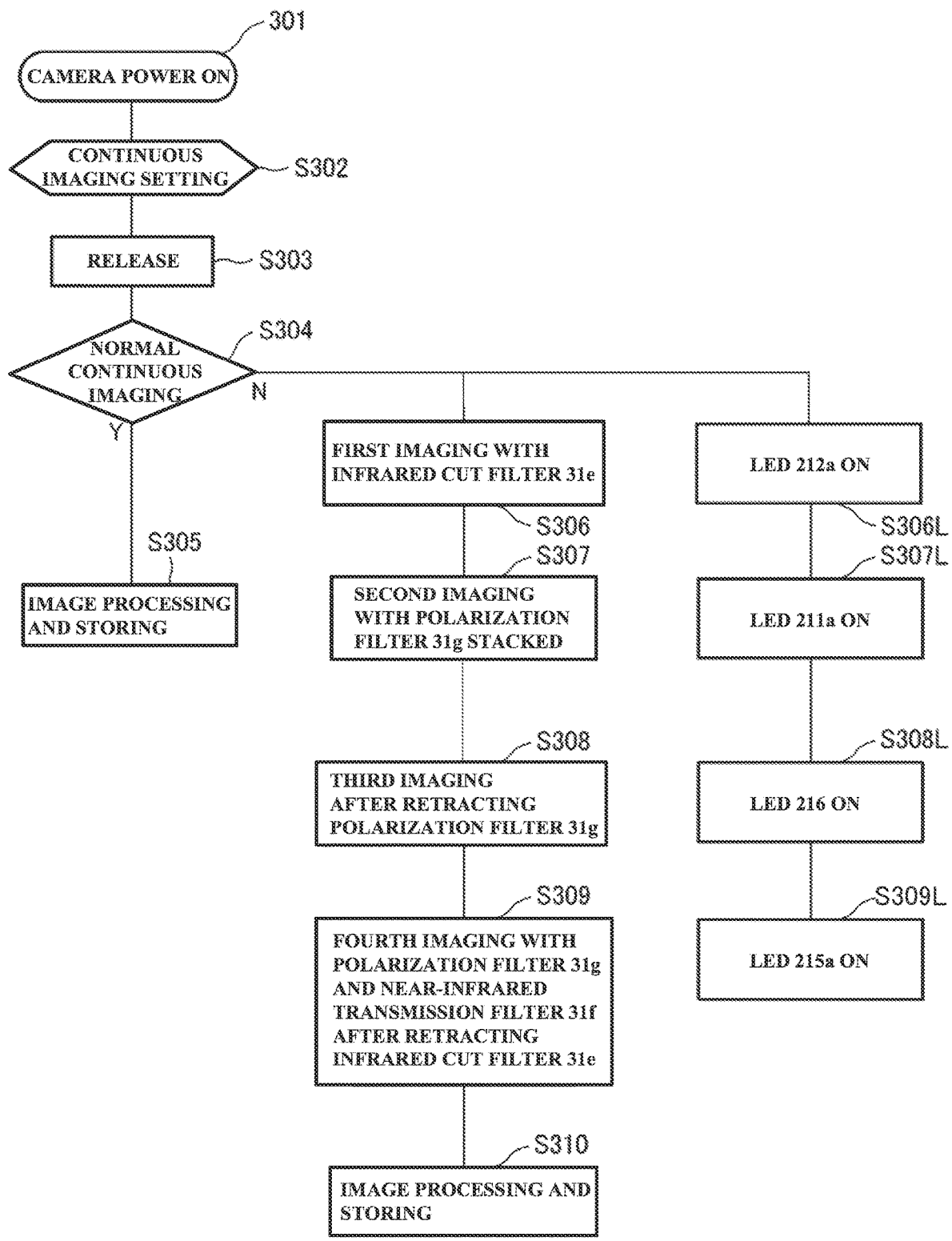
FIG. 20 is a view explaining the relationship between the operations of the filter unit and the operations of the light unit according to Embodiment 3.

Next, the operation flow of the dermoscopy camera 30 is described while referencing FIGS. 19 and 20. FIG. 19 illustrates the operation flow of the filter unit 31 in a case in which the filter unit 31 is switched alone. FIG. 20 illustrates the relationship between the operations of the filter unit 31 and the operations of the light unit 23 for a case in which the filter unit 31 is switched in conjunction with the light unit 23. Note that, the elements that are the same as in Embodiment 1 and Embodiment 2 are marked with the same reference numerals given in each embodiment.

As illustrated in FIG. 19, first, the user sets the power button of the dermoscopy camera 30, which is provided on the controller 2, to the ON state (step S301). Next, the user operates the controller 2 to perform continuous imaging (step S302). Then, the user presses the shutter button 2a, and the dermoscopy camera 30 is release operated (step S303).

If the switch 18 is in the OFF state, that is, normal continuous imaging is set to YES at the time of release (step S304; Y), the filter unit 31 does not switch the plurality of filters 31A, and the dermoscopy camera 30 continuously captures images of the subject and image-processes and stores the continuously captured images (step S305).

If the switch 18 is in the ON state, that is, normal continuous imaging is set to NO at the time of release (step S304; N), the filter unit 31 positions the infrared cut filter 31e on the optical axis of the imaging lens system 21d, and the dermoscopy camera 30 performs a first imaging (step S306). Next, the filter unit 31 stacks the polarization filter 31g on the infrared cut filter 31e, thereby positioning the polarization filter 31g and the infrared cut filter 31e on the optical axis of the imaging lens system 21d, and the dermoscopy camera 30 performs a second imaging (step S307).

Next, the filter unit 31 retracts the polarization filter 31g from the optical axis of the imaging lens system 21d, and the dermoscopy camera 30 performs a third imaging while the infrared cut filter 31e is positioned on the optical axis of the imaging lens system 21d (step S308). Then, the filter unit 31 retracts the infrared cut filter 31e from the optical axis of the imaging lens system 21d, stacks the near-infrared transmission filter 31f on the polarization filter 31g, thereby positioning the near-infrared transmission filter 31f and the polarization filter 31g on the optical axis of the imaging lens system 21d, and the dermoscopy camera 30 performs a fourth imaging (step S309). Finally, the images captured by the series of continuous imaging are image processed and stored (step S310).

Note that the addition of step S308 and step S309 to the continuous imaging by a single shutter operation is optional. The user (doctor), for example, can set whether to add step S308 and step S309 to the continuous imaging as desired.

FIG. 20 illustrates the relationship between the operations of the filter unit 31 and the operations of the light unit 23. The light unit 23 turns on the LED 212a that is not covered by a polarization film in response to step S306 of the operations of the filter unit 31 (step S306L). The light unit 23 turns on the LED 211a that is covered by the polarization filter 213 in response to step S307 of the operations of the filter unit 31 (step S307L). The light unit 23 turns on the normal imaging LED 216 in response to step S308 of the operations of the filter unit 31 (step S308L). The light unit 23 turns on the LED 215a that emits near-infrared light in response to step S309 of the operations of the filter unit 31 (step S309L).

Modified Example of Embodiment 3

Figure 21:
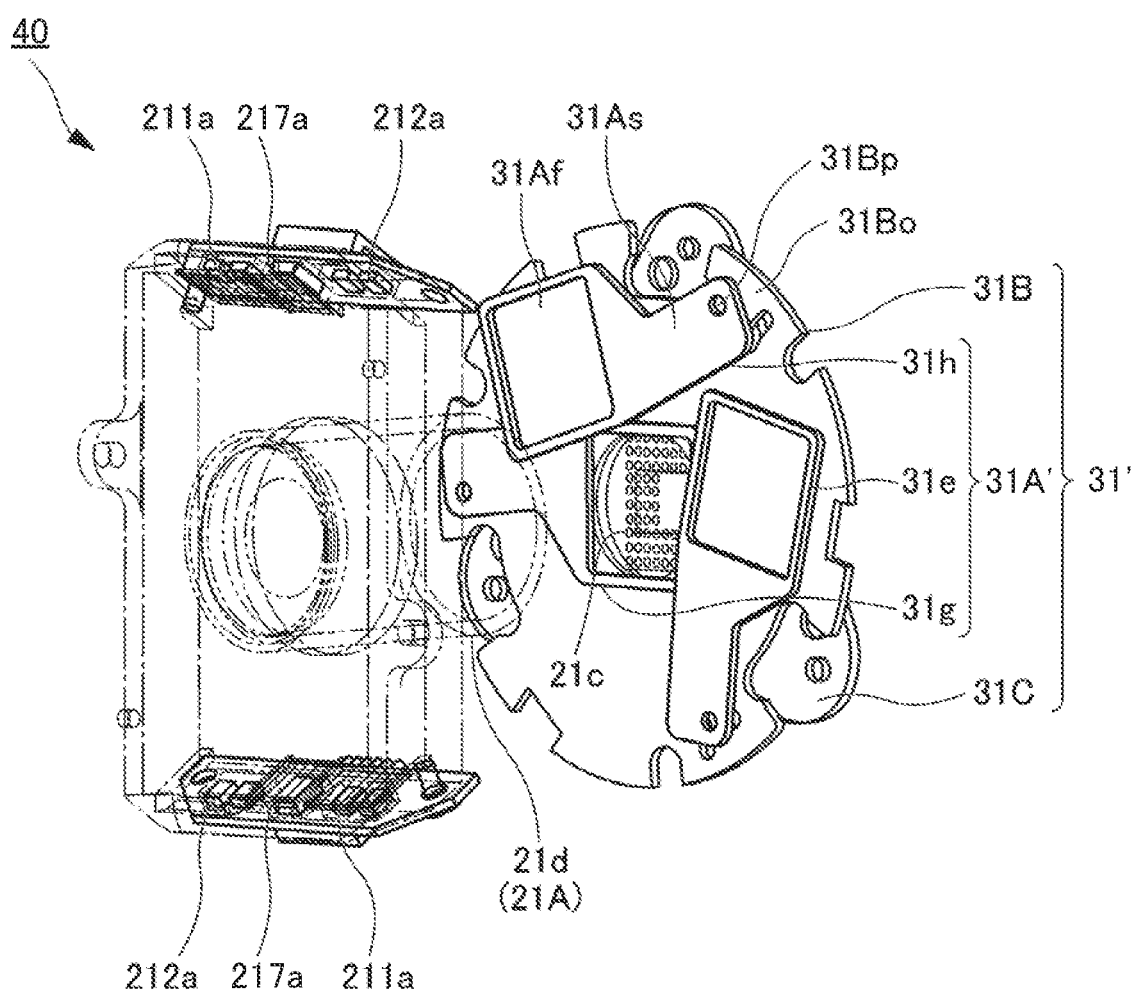
FIG. 21 is a partial perspective view of an imaging device according to a modified example of Embodiment 3.
Figure 22:
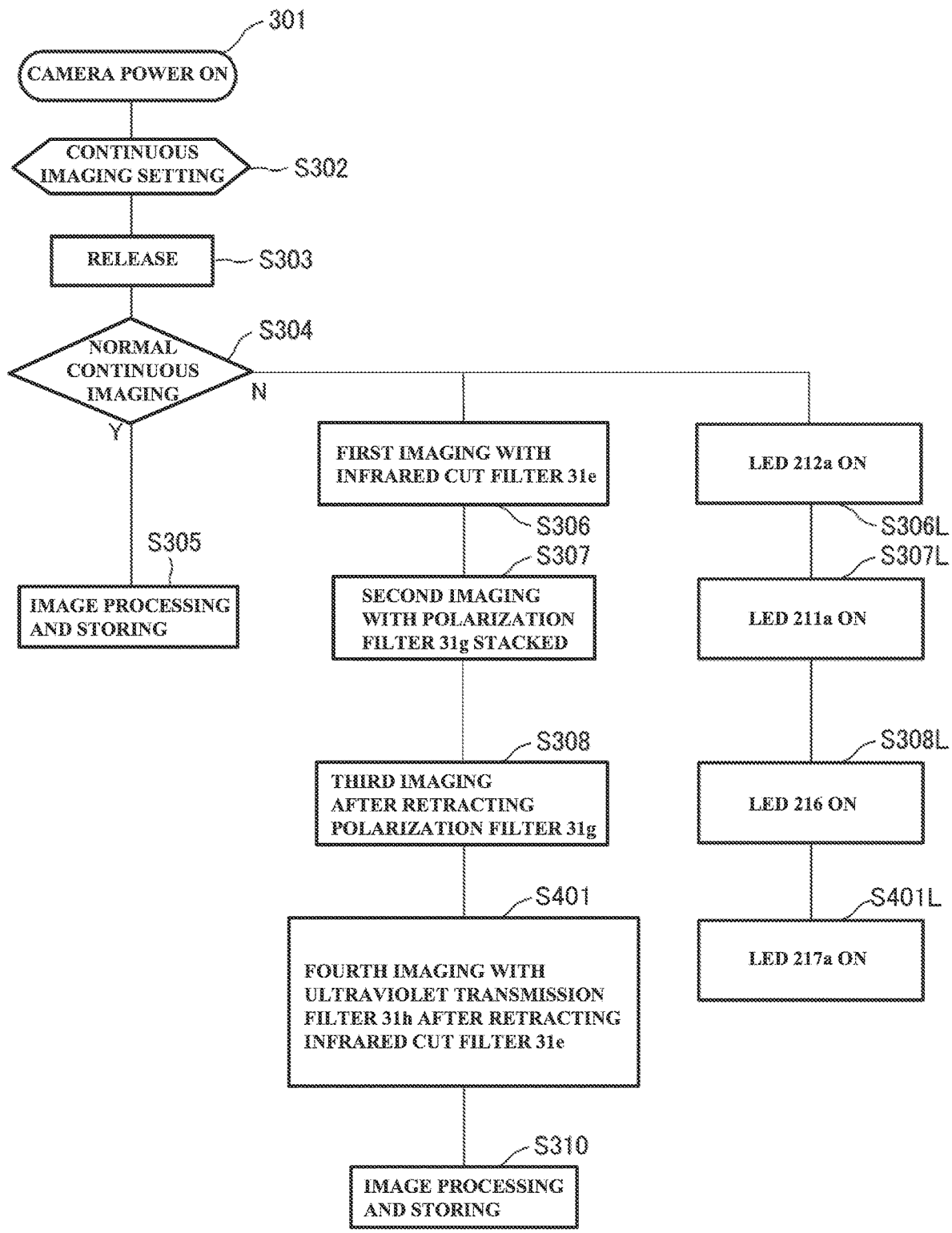
FIG. 22 is a drawing explaining the operation flows of the filter unit and the light unit according to a modified example of Embodiment 3.

Next, a dermoscopy camera 40 (imaging device) according to a modified example of Embodiment 3 is described while referencing FIGS. 21 and 22. As described above, the dermoscopy camera 40 differs mainly from the dermoscopy camera 30 according to Embodiment 3 in that an LED 217a that emits ultraviolet light is used instead of the LED 215a that emits near-infrared light, and an ultraviolet transmission filter 31h is used instead of the near-infrared transmission filter 31f. The other configurations of the dermoscopy camera 40 are the same as the dermoscopy camera 30. The following description focuses on the differences with Embodiment 3.

The LED 217a that emits ultraviolet light is arranged in place of the LED 215a, at the position where the LED 215a is arranged in FIGS. 10, 12, and 13. The LED 217a differs from the LED 215a in that the LED 217a is not covered by a polarization filter such as the polarization filter 214.

As illustrated in FIG. 21, the ultraviolet transmission filter 31h of the filter unit 31' includes a filter 31Af and a shaft 31As in the same manner as the near-infrared transmission filter 31f of Embodiment 3. The ultraviolet transmission filter 31h is pivotably supported by the filter attachment plate 31B so as to be rotatable with respect to the filter attachment plate 31B. Specifically, a plurality of filters 31A' including the infrared cut filter 31e, the polarization filter 31g, and the ultraviolet transmission filter 31h can be positioned independently of each other on the optical axis of the imaging lens system 21d or retracted independently of each other from the optical axis of the imaging lens system 21d.

FIG. 22 illustrates the operation flow of a case in which, in the dermoscopy camera 40, a filter unit 31' is switched in conjunction with a light unit that includes the ultraviolet light LED 217a and the like. In FIG. 22, the processing contents that are the same as in the operation flow of FIG. 20 described in Embodiment 3 are marked with the same step numbers. The operation flow in this modified example differs from FIG. 20 only in that step S401 is executed instead of step S309 and step S401L is executed instead of step S309L. As such, only the processing content of steps S401 and S401L will be described.

In step S401 that follows step S308, the filter unit 31' retracts the infrared cut filter 31e from the optical axis of the imaging lens system 21d and, thereafter, positions only the near ultraviolet transmission filter 31h of the plurality of filters 31A' on the optical axis of the imaging lens system 21d, and the dermoscopy camera 40 performs the fourth imaging. In step S401L that follows step S308L, in response to step S401, the light unit 23 turns on the LED 217a that emits ultraviolet light for the fourth imaging Thus, the filter unit 31' and the light unit 23 of the dermoscopy camera 40 of the modified example of Embodiment 3 can demonstrate the same advantageous effects as the dermoscopy camera 30, the filter unit 31, and the light unit 23 of Embodiment 3.

Advantageous Effects of the Embodiments

As described above, the dermoscopy cameras 10 and 20 according to Embodiments 1 and 2 can, with simple configurations and operations, capture images with unpolarized light illumination that enable the observation of the skin surface, and images with polarized light illumination that enable the observation of the interior of the skin.

The dermoscopy cameras 10 and 20 can, by a single shutter operation, switch between the light sources of the light unit 3, that is, switch between the LED 11a for illuminating the subject with polarized light and the LED 12a for illuminating the subject with unpolarized light, and perform continuous imaging. Therefore, in the dermoscopy cameras 10 and 20, the need to replace the light sources of the light unit 3 is eliminated.

The dermoscopy cameras 10 and 20 can include, as light sources for dermoscopy imaging, many types of light sources including LEDs that emit visible light, LEDs that emit ultraviolet light, LEDs that emit near-infrared light, and the like. Therefore, with the dermoscopy cameras 10 and 20, it is possible to switch between the light sources of the light unit 3 at a high-speed when performing continuous imaging and, as a result, imaging in which multiple types of light sources are used can be carried out by a single shutter operation.

In conventional dermoscopy cameras, two images are captured in two operations. Consequently, differences caused by exposure, white balance, and external light, and deviations in the angle of view occur. The dermoscopy cameras 10 and 20 perform continuous imaging, in which the light source of the light unit 3 is switched at high-speed, by a single shutter operation. As such, it is possible to capture a plurality of images, which are not affected by differences caused by exposure, white balance, external light, and the like, at the same angle of view and the same magnification while varying the light that illuminates the subject (for example, polarized light and unpolarized light). As a result, a plurality of images that can be easily compared can be obtained. Moreover, the time needed for diagnosing can be shortened.

In the dermoscopy cameras 30 and 40, the switching of the lighting pattern that uses the LED 212a that is not covered by a polarization film and the LED 211a that is covered by the polarization filter 213 is combined with the position of the polarization filter 31g (whether the polarization filter 31g is positioned on the optical axis of the imaging lens system 21d). As a result, it is possible to switch between imaging in which the subject is illuminated with polarized light and imaging in which the subject is illuminated with unpolarized light.

In the dermoscopy cameras 30 and 40, each of the plurality of filters 31A, including the polarization filter 31g, can, by a rotation operation, be positioned independently of each other on the optical axis of the imaging lens system 21d or be retracted independently of each other from the optical axis of the imaging lens system 21d. Therefore, in dermoscopy imaging, normal imaging (clinical imaging), and other imaging, the dermoscopy cameras 30 and 40 can select and optionally combine the required filters. Moreover, with the dermoscopy cameras 30 and 40, each of the plurality of filters 31A are moved by rotating and, as such, the operating time and the operating distance between each of the plurality of filters 31A and the optical axis of the imaging lens system 21d can be made uniform. Furthermore, with the dermoscopy cameras 30 and 40, the filter units 31 and 31' are provided behind the imaging lens system 21d. As such, implementation efficiency can be improved without increasing the size (in particular, the thickness in the depth direction) of the lens unit 21A. Note that the dermoscopy cameras 30 and 40 demonstrate the same advantageous effects as the advantageous effects described for the dermoscopy cameras 10 and 20.

Modifications of the Embodiments

The present disclosure is not limited to the embodiments described above and various modifications and uses are possible. It is sufficient that the light units 3 and 23 are arranged so as to cover the front of the imaging lens systems 1d and 21d when imaging. In one example, the light units 3 and 23 may be rotatably attached to the camera bodies 1 and 21. The light units 3 and 23 may be slideably attached to the camera bodies 1 and 21. The imaging lens systems 1d and 21d may be a fixed focus lens in consideration of the use of the dermoscopy cameras 10, 20, 30, and 40.

When controlling the lighting pattern of the light sources of the light units 3 and 23 on the basis of the lighting state of the power lamp 17, the light units 3 and 23 may execute more lighting patterns by increasing the emitted colors of the power lamp 17, increasing or decreasing the amount of emitted light of the power lamp 17, increasing the lighting variations (blinking and the like), and the like. As a result, the light units 3 and 23 can control light source lighting patterns of greater complexity.

In the embodiments described above, the power lamp 17 is used to control the lighting pattern, but an existing component provided in the camera bodies 1 and 21 may be used to control the lighting pattern. In one example, a strobe, a display monitor, or the like provided in the camera bodies 1 and 21 may be used in the control, and the light units 3 and 23 may detect changes in the strobe, the display monitor, and the like. Additionally, the camera bodies 1 and 21 may be electrically connected to the light units 3 and 23 to control the lighting pattern.

The light sources of the light units 3 and 23 are not limited to LEDs, and other light sources may be implemented. The light sources of the light units 3 and 23 may be high-brightness lamps (for example, halogen lamps), semiconductor light-emitting devices, organic electroluminescence, or the like.

The LED 216 is not limited to an LED that emits white light, and may be implemented as a light source that emits blue light, a light source that emits green light, or the like. The light units 3 and 23 may include a plurality of light sources that emit light of different wavelength regions (for example, blue light and green light) at visible light wavelengths. By illuminating the subject with light of different wavelength regions at visible light wavelengths and imaging, different images at visible light wavelengths can be obtained. Additionally, by comparing or stacking different images at visible light wavelengths, the examination and diagnosis of the skin disease site can be facilitated.

In the embodiments described above, the dermoscopy cameras 10, 20, 30, and 40 performed continuous imaging by a single shutter operation, but the dermoscopy cameras 10, 20, 30, and 40 may perform continuous imaging by two high-speed shutter operations, a double tap, or the like.

The imaging device according to the present disclosure is not limited to the imaging device for dermoscopy imaging such as the dermoscopy cameras 10, 20, 30, and 40 of the embodiments described above. In general, the present disclosure can be applied to an imaging device that images by being brought into contact with the subject, namely, a close-up camera or the like.

The display of the dermoscopy camera 10 and the display 22C of the dermoscopy camera 20 may include a touch panel. For example, the controller 22 may be configured such that the display 22C that includes the touch panel can separate from the controller 22. In this case, the display 22C and the controller 22 communicate bidirectionally with each other using existing communication technology. The user can perform the various settings, shutter operations, and the like by operating the display 22C.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

INDUSTRIAL APPLICABILITY

The present invention is particularly useful for obtaining, by a simple operation, a plurality of images in which a disease site can be easily observed.

REFERENCE SIGNS LIST

1 Camera body
1a Housing
1b Circuit wiring board
1c Imaging element
1d Imaging lens system
2 Controller
2a Shutter button
3 Light unit
3A First cover
3B Second cover
4 Attachment stay
5 Stay fixing screw
6 Cover member
7 Light emitter
8 Power button
9 Battery
10 Dermoscopy camera (imaging device)
11 LED board
11a LED (first light source)
12 LED board
12a LED (second light source)
13 Polarization filter
14 Polarization filter
15 Photosensor (light receiving element)
15a Window
16 LED control board
17 Power lamp
18 Switch
20 Dermoscopy camera (imaging device)
21 Camera body
21A Lens unit
21B Frame
21a Housing
21b Circuit wiring board
21c Imaging element 21d Imaging lens system
21e Infrared cut filter
21f Near-infrared transmission filter
21g Polarization filter
21h Flexible circuit board
22 Controller
22A Body
22B Circuit board
22C Display
Light unit
23A First cover
23B Second cover
26 Cover member
27 Light emitter
28 Wire
28a Terminal
29 Wire
29a Terminal
30 Dermoscopy camera (imaging device)
31 Filter unit
31' Filter unit
31A Plurality of filters
31A' Plurality of filters
31B Filter attachment plate
31C Fitter
31e Infrared cut filter
31f Near-infrared transmission filter
31g Polarization filter
31h Ultraviolet transmission filter
31Af Filter
31As Shaft
31Bo Outer periphery
31Bp Pin
40 Dermoscopy camera (imaging device)
211a LED (first light source)
212a LED (second light source)
213 Polarization filter
214 Polarization filter
215a LED
216 LED
217a LED
θx Vertical angle of view
θy Horizontal angle of view

The invention claimed is:

1. An imaging device configured to image a disease site as a subject, the imaging device comprising:
a processor;
a camera body;
a first filter; and
a second filter having characteristics different from characteristics of the first filter,
wherein the processor is configured to, in response to a single image capture instruction operation, perform both of:
a first imaging process of imaging, by the camera body, a subject illuminated with light in a first state in which the first filter is positioned on an optical axis of the camera body; and
a second imaging process of imaging, by the camera body, the subject illuminated with light in a second state in which the second filter is positioned on the optical axis of the camera body, and
wherein one of the first imaging process and the second imaging process is performed in a state in which both of the first filter and the second filter are simultaneously positioned on the optical axis of the camera body.

2. The imaging device according to claim 1, further comprising:
a filter unit that includes the first filter and the second filter,
wherein the processor controls the filter unit to position at least one of the first filter and the second filter on the optical axis of the camera body depending on whether the first imaging process or the second imaging process is performed.

3. The imaging device according to claim 2, wherein the filter unit is configured such that each of the first filter and the second filter is positionable on the optical axis of the camera body and retractable from the optical axis of the camera body by a rotation operation.

4. The imaging device according to claim 2, wherein:
the processor controls the filter unit to position the first filter on the optical axis of the camera body in the first imaging process, and
the processor controls the filter unit to position both of the first filter and the second filter on the optical axis of the camera body in the second imaging process.

5. The imaging device according to claim 1, wherein:
the first filter comprises one of an infrared cut filter and a polarization filter, and
the second filter comprises the other of the infrared cut filter and the polarization filter.

6. The imaging device according to claim 1, wherein:
the first filter comprises one of a near-infrared transmission filter and a polarization filter, and
the second filter comprises the other of the near-infrared transmission filter and the polarization filter.

7. The imaging device according to claim 1, wherein:
the first filter comprises one of a ultraviolet transmission filter and a polarization filter, and
the second filter comprises the other of the ultraviolet transmission filter and the polarization filter.

8. The imaging device according to claim 1, further comprising:
a first light source; and
a second light source having characteristics different from characteristics of the first light source,
wherein:
the subject is illuminated with light from the first light source in the first imaging process, and
the subject is illuminated with light from the second light source in the second imaging process.

9. The imaging device according to claim 8, wherein:
one of the first light source and the second light source emits polarized light, and
the other of the first light source and the second light source emits unpolarized light.

10. The imaging device according to claim 8, further comprising:
a light unit that includes the first light source and the second light source,
wherein the processor controls the light unit to illuminate the subject with the light from the first light source in the first imaging process, and to illuminate the subject with the light from the second light source in the second imaging process.

11. The imaging device according to claim 10, wherein:
the light unit further includes a switch, and
the processor controls the light unit to illuminate the subject with the light from the first light source in the first imaging process, and to illuminate the subject with the light from the second light source in the second imaging process, when the switch is in an ON state.

12. The imaging device according to claim 10, wherein:
in the first imaging process, the processor (i) controls the camera body to image the subject in the first state in which the subject is illuminated with the light from the first light source, and then (ii) controls the light unit to turn off the first light source, and
in the second imaging process, after the first light source is turned off in the first imaging process, the processor (i) controls the light unit to turn on the second light source, and (ii) controls the camera body to image the subject in the second state in which the subject is illuminated with the light from the second light source.

13. The imaging device according to claim 8, wherein the first light source and the second light source are provided so as to oppose each other across the optical axis of the camera body.

14. The imaging device according to claim 10, wherein:
the light unit includes at least two of a light source that emits visible light, a light source that emits ultraviolet light, and a light source that emits near-infrared light, as the first light source and the second light source, and
both of the first imaging process and the second imaging process are performed in response to the single image capture instruction operation while illuminating the subject with at least two of the visible light, the ultraviolet light, and the near-infrared light.

15. The imaging device according to claim 1, further comprising:
a shutter button,
wherein the processor is configured to, in response to a single operation of the shutter button as the single image capture instruction operation, perform both of the first image process and the second image process.

16. An imaging method for an imaging device configured to image a disease site as a subject, the imaging device including a processor, a camera body, a first filter, and a second filter, the first filter and the second filter having mutually different characteristics, and the method comprising:

in response to a single image capture instruction operation, performing both of:
a first imaging process of imaging, by the camera body, a subject illuminated with light in a first state in which the first filter is positioned on an optical axis of the camera body; and
a second imaging process of imaging, by the camera body, the subject illuminated with light in a second state in which the second filter is positioned on the optical axis of the camera body,
wherein one of the first imaging process and the second imaging process is performed in a state in which both of the first filter and the second filter are simultaneously positioned on the optical axis of the camera body.

17. A non-transitory computer-readable storage medium storing a program executable by a processor of an imaging device, the imaging device being configured to image a disease site as a subject, the imaging device further including a camera body, a first filter, and a second filter, the first filter and the second filter having mutually different characteristics, and the program being executable to control the processor to perform processes comprising:
in response to a single image capture instruction operation, performing both of:
a first imaging process of imaging, by the camera body, a subject illuminated with light in a first state in which the first filter is positioned on an optical axis of the camera body; and
a second imaging process of imaging, by the camera body, the subject illuminated with light in a second state in which the second filter is positioned on the optical axis of the camera body,
wherein one of the first imaging process and the second imaging process is performed in a state in which both of the first filter and the second filter are simultaneously positioned on the optical axis of the camera body.

* * * * *